(12) United States Patent
Imperiali et al.

(10) Patent No.: US 7,101,667 B2
(45) Date of Patent: Sep. 5, 2006

(54) LANTHANIDE BINDING TAGS

(75) Inventors: Barbara Imperiali, Cambridge, MA (US); Karen N. Allen, Boston, MA (US); Katherine J. Franz, Cambridge, MA (US)

(73) Assignees: Massachusetts Institute of Technology, Cambridge, MA (US); Trustees of Boston University, Boston, MA (US)

( * ) Notice: Subject to any disclaimer, the term of this patent is extended or adjusted under 35 U.S.C. 154(b) by 455 days.

(21) Appl. No.: 10/235,561

(22) Filed: Sep. 5, 2002

(65) Prior Publication Data

US 2003/0228622 A1 Dec. 11, 2003

Related U.S. Application Data

(60) Provisional application No. 60/318,220, filed on Sep. 7, 2001.

(51) Int. Cl.
*C12Q 1/68* (2006.01)
*C12Q 1/37* (2006.01)
*G01N 33/53* (2006.01)
*A01K 38/00* (2006.01)

(52) U.S. Cl. .............. 435/6; 435/23; 435/24; 435/968; 435/320.1; 530/300

(58) Field of Classification Search ............... 435/6, 435/23, 24, 968, 320.1; 530/300
See application file for complete search history.

(56) References Cited

FOREIGN PATENT DOCUMENTS

| WO | WO 02/11672 | 2/2002 |
| WO | WO 02/11672 A2 * | 2/2002 |

OTHER PUBLICATIONS

Feeny et al, J. Biomolecular NMR,V.21(1), p. 41–8, (Sep. 2001).*
Aime S. et al., "Non–Covalent Conjugates Between Cationic Polyamino Acids and Gdlll Chelates: A Route For Seeking Accumulation of MRI–Contrast Agents At Tumor Targeting Sites," *Chemistry* 6(14):2609–17 (2000).
Allegrozzi M. et al., "Lanthanide–Induced Pseudocontact Shifts For Solution Structure Refinements Of Macromolecules In Shells Up 40A From The metal Ion," *J. Am. Chem. Soc.*, 122:4154–4161 (2000).
Anderson S.A. et al., "Magnetic Resonance Contrast Enhancement of Neovasculature With Alpha(v)beta(3)–targeted Nanoparticles," *Magn. Reson. Med.* 44(3):433–9 (2000).
Barbieri R. et al., "Paramagnetically Induced Residual Dipolar Couplings For Solution Structure Determination Of Lanthanide Binding Proteins," *J. Am. Chem. Soc.*, 124(19):5581–5587 (2002).
Carter C.W. et al., "Protein Crystallization Using Incomplete Factorial Experiments," *J. Biol. Chem.*, 254(23):12219–12223 (1979).
Clainche L.L. et al., "Engineering New Metal Specificity In EF–Hand Peptides," *JBIC* (2002).
Connelly P.R. et al., "Thermodynamics of Protein–Peptide Interactions in the Ribonuclease S System Studied by Titration Calorimetry," *Biochemistry*, 29:6108–6114 (1990).

(Continued)

*Primary Examiner*—Louise N. Leary
(74) *Attorney, Agent, or Firm*—Brinks Hofer Gilson & Lione

(57) ABSTRACT

The present invention provides lanthanide binding tags (LBT) that selectively complex trivalent lanthanide (Ln) ions and afford stable complexes with desirable physical properties, including at least one of fluorescence and anomalous x-ray scattering.

21 Claims, 3 Drawing Sheets

OTHER PUBLICATIONS

Corpet F. et al., "Multiple Sequence Alignment With Hierarchical Clustering," *Nucleic Acid Research*, 16(22):10881–90(1988).

Cudney B. and Patel S., "Screening and Optimization for Macromolecular Crystal Growth," *Acta Cryst.*., D50:414–423 (1994).

Drenth J, *Principles of Protein X–Ray Crystallography*, Springer–Verlag (1994).

Gudgin Dickson E.F., Pollak A., and Diamandis E.P., "Ultrasensitive Bioanalytical Assays Using Time–Resolved Fluorescence Detection," *Pharmac. Ther.*, 66:207–235 (1995).

Gupta H. and Weissleder R., "Targeted Contrast Agents in MR Imaging," *Magn. Reson. Imaging Clin. N. Am.* 4(1):171–184 (1996).

Halliday and Resnick, *Fundamentals of Physics*, 2nd Ed., John Wiley and Sons, Inc. (1981).

Higgins D.G. and Sharp P.M., "CLUSTAL: A Package For Performing Multiple Sequence Alignment On A Microcomputer" *Gene*, 73:237–244 (1988).

Higgins D.G and Sharp P.M., "Fast and Sensitive Multiple Sequence Alignments On A Computer," *CABIOS*, 5(2): 151–153 (1989).

Hill I.E. et al., "Detection Of Calcium Binding Proteins On Polyacrylaminde Gels Using Time–Resolved Lanthanide Luminescence Photography," *Anal. Biochem.*, 216:439–443 (1994).

Hogue C.W.V. et al., "Comparison Of Terbium (III) Luminescence Enhancement in Mutants Of EF Hand Calcium Binding Proteins," J. Biol. Chem., 267(19):13340–13347 (1992).

Huang X. et al., "Parallelization Of A Local Similarity Algorithm," *Computer Applic. Biosci.*, 8(2): 155–65 (1992).

Jancarik J. and Kim S.–H., "Sparse Matrix Sampling: A Screening Method For Crystalization Of Proteins," *J. Appl. Cryst.*, 24, 409–411 (1991).

Kanellis P. et al., "Synthetic Peptide Analogs Of Skeletal Tropin C: Fluorescence Studies of Analogs of the Low–Affinity Calcium–Binding Site," *Arch. Biochem. Biophys.*, 220(2):530–540 (1983).

Keleman B.R. et al., "Hypersensitive Substrate for Ribonucleases," *Nucleic Acid Res.*, 27(18):3696–3701 (1999).

Kim J.–S. & Raines R.T., "Peptide Tags for a Dual Affinity Fusion System," *Anal. Biochem.*, 219:165–166 (1994).

Kraynov V.S. et al., "Localized Rac activation Dynamics Visualized in Living Cells," *Science*, 290:333–337 (2000).

Lopez M.M. et al., "The Enthalpy of the Alanine Peptide Helix Measured by Isothermal Titration Calorimetry Using Metal–Binding to Induce helix Formation," *Proc. Natl. Acad. Sci. USA*, 99:1298–1303 (2002).

Ma C. and Opella S.J., "Lanthanide Ions Bind Specifically To An Added 'EF–Hand' And Orient A Membrane Protein In Micelles For Solution NMR Spectroscopy" *J. Magnetic Resonance*, 146:381–384 (2000).

MacManus J.P. et al., "Terbium Luminescence in Synthetic Peptide Loops From Calcium–Binding Proteins With Different Energy Donors," *J. Biol. Chem.*, 265(18): 10358–10366 (1990).

McRee DE, *Practical Protein Crystallography*, Academic Press: Boston (1993).

Meyers E.W. and Miller W., "Optimal Alignments in Linear Space," *Computer Applic. Biol. Sci.*, 4(1):11–17 (1998).

Mitra R.D. et al., "Fluoresence Resonance Energy Transfer Between Blue–Emitting And Red–Shifted Excitation Derivatives of the Green Fluorescent protein," *Gene*, 173: 13–17 (1996).

Needleman S.B. and Wunsch C.D., "A General Method Applicable to the Search for Similarities in the Amino Acid Sequence of Two Proteins," *J. Mol. Biol.*, 48:443–453 (1970).

Opsahl et al., "Tumor imaging with a macromolecular paramagnetic contrast agent: gadopentetate dimeglumine–polylysine," *Acad. Radiol.*, 2(9):762–7 (1995).

Park S.–H. and Raines R.T., "Green Fluorescent Protein as a Signal for protein—Protein Interactions," *Protein Sci.*, 6:2344–49 (1997).

Pearson W.R., "Using the FASTA Program to Search protein and DNA Sequence Databases," *Methods Molec. Biol.*, 24:307–31(1994).

Pearson W.R. and Lipman D.J., "Improved Tools for Biological Sequence Comparison," *Proc. Nat. Acad. Sci. USA*, 85:2444–2448 (1988).

Pidcock E. and Moore G.R., "Structural Characteristics Of Protein Binding Sites For Calcium And Lanthanide Ions," JBIC, 6(516):479–489 (2001).

Raines R.T., "Ribonuclease A," *Chem. Rev.*, 98:1045–1066 (1998).

Richardson F.S., "Terbium(III) and Europium(III) Ions as Luminescent probes and Stains for Biomolecular Systems," *Chem. Rev.*, 82:541–552 (1982).

Sakash J.B. and Kantrowitz E.R., "The Contribution of Individual Interchain Interactions to the Stabilization of the T and R States for *Escherichia coli* Aspartate Transcarbamoylase," *J. Biol. Chem.*, 275:28701–28707 (2000).

Selvin P.R., "Principles And Biophysical Applications Of Lanthanide–Based Probes," *Annu. Rev. Biophys. Biomol. Struct.*, 31:275–302 (2002).

Smith T.F. and Waterman M.S., "Comparison of Biosequences," *Adv. Appl. Math.*, 2:482 (1981).

Vazquez–Ibar J.L. et al., "Engineering A Terbium–Binding Site Into An integral Membrane Protein For Luminescence Energy Transfer," PNAS, 99(6):3487–3492 (Mar. 19, 2002).

Veglia G. and Opella J., "Lanthanide Ion Binding To Adventitious Sites Aligns Membrane Proteins In Micelles For Solution NMR Spectroscopy," *J. Am. Chem. Soc.*, 122:11733–34 (2000).

Wild J.R. et al., "In the Presence of CTP, UTP Becomes as Allosteric Inhibitor of Aspartate Transcarbamoylase," *Proc. Natl. Acad. Sci. USA*, 86:46–50.

Wlodawer A. et al., "Conserved Folding in Retroviral Proteases: Crystal Structure of a Synthetic HIV–1 Protease," *Science*, 245:616–621 1989.

Nitz M. et al., "A Powerful Combinational Screen to Identify High Affinity Terbium(III)–Binding Peptides," *ChemBioChem*, 4 (2003).

Franz K.J. et al., "Lanthanide–Binding Tags as Versatile Protein Coexpression Probes," (2003).

\* cited by examiner

HIS-LBT-Ub

LANTHANIDE BINDING TAGS

This application claims the benefit of Provisional Application No. 60/318,220, filed Sep. 7, 20001.

BACKGROUND OF THE INVENTION

The present invention provides lanthanide binding tags (LBT) that selectively complex trivalent lanthanide (Ln) ions and afford stable complexes with desirable physical properties, including at least one of fluorescence and X-ray scattering and anomalous X-ray scattering. These LBTs are useful as probes for applications in analytical biochemistry, biophysics, biotechnology, medicine, and proteomics.

One notable use is in the arena of determining protein structures. With the release of the sequence of the human genome, determining the structure of proteins of the genome-wide scale is a formidable task. Traditionally, each target gene is cloned into an expression vector, expressed with the use of a single set of conditions, and the resulting protein in then purified. With this protein in hand, a number of basic screens for crystallization are used, followed by further screening, if necessary, to optimize crystal quality. Lastly, the best crystal(s) are used for diffraction analysis.

Using conventional methods, the throughput of macromolecular 3D structure determination can be improved only by increasing the person-hours of work. As a consequence, academic and industry-based researchers have initiated research and development programs to develop high-throughput (HT) structure determination process pipelines. HT structural biology requires development of methods and reagents to streamline and automate the process of protein structure determination.

The early steps in the pipeline can capitalize on the HT technologies developed during genomic sequencing efforts. Robotic liquid handling and colony picking procedures, as well as automated sequencing, can easily be adapted for the cloning and expression steps. As these impediments are removed, other processes become rate limiting. For example, once sufficient quantities of purified protein are obtained, crystals suitable for x-ray diffraction must be grown and phase information obtained from these crystals in order to determine the structure. Lastly, the diffraction data collection phase determination, and analysis steps must be automated, streamlined, and made user-independent.

Along with other applications described herein, the LBTs of the present invention can be easily integrated into the covalent architecture of the protein products of the genes of interest and used to facilitate aspects of structure and function determining processes, including x-ray diffraction structure determination.

BRIEF SUMMARY OF THE INVENTION

The present invention provides LBTs that can be used to label proteins with a fluorescent tag, to facilitate the phase determination for crystallized proteins, and to image proteins. The LBTs of the present invention bind lanthanide ions with affinities in the nM to µM range. A major advantage of the LBTs of the present invention is their multitasking nature; they can be used to investigate sequential processes in structural and functional genomics.

LBTs comprise short peptide sequences (fewer than 20 amino acids) that are optimized to bind trivalent lanthanide ($Ln^{3+}$) ions. Because the tags are built from encoded amino acids, LBTs can be introduced as co-expression tags at the DNA level to create fusion proteins. Post-expression addition of a particular Ln ion provides the "function" of the LBT. The LBT sequence imparts on the fusion protein a built-in and site-specific fluorophore that can be used for monitoring protein expression and purification, and for assaying protein/protein and protein/ligand interactions. Lanthanides also provide excellent X-ray scattering power; therefore co-expression of a target protein with an LBT will accelerate the determination of protein X-ray structures by providing an intrinsic, ordered heavy atom for phase determination. Additionally, the paramagnetic lanthanides can be used as NMR probes of protein structure in solution.

Individually, the above applications are feasible using existing technologies; however, a unique protein construct is required for each type of experiment. There currently does not exist a convenient protein tag that encompasses the breadth of applications proposed for the LBTs. The LBTs of the present invention allow each of the above applications to be realized with a single construct.

DETAILED DESCRIPTION OF THE INVENTION

I. Definitions

Figure 1:
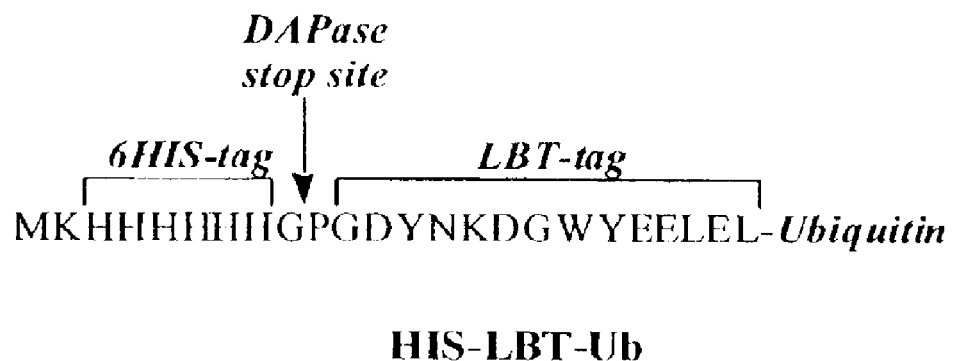
FIG. 1 is a schematic showing the expression and proteolytic processing of LBT-Ubiquitin conjugates.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "nucleic acid" refers to a deoxyribonucleotide or ribonucleotide polymer in either single- or double-stranded form, and, unless otherwise limited, encompasses known analogs of natural nucleotides that can function in a similar manner as naturally occurring nucleotides. It will be understood that when a nucleic acid molecule is represented by a DNA sequence, this also includes RNA molecules having the corresponding RNA sequence in which "U" replaces "T."

The term "recombinant nucleic acid molecule" refers to a nucleic acid molecule which is not naturally occurring, and which comprises two nucleotide sequences which are not naturally joined together. Recombinant nucleic acid molecules are produced by artificial recombination, e.g., genetic engineering techniques or chemical synthesis.

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

The term "expression control sequences" refers to nucleotide sequences that regulate the expression of a nucleotide sequence to which they are operatively linked. Expression control sequences are "operatively linked" to a nucleotide sequence when the expression control sequences control and regulate the transcription and, as appropriate, translation of the nucleotide sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the MRNA, and stop codons.

The term "probe" refers to a substance that specifically binds to another substance (a "target"). Probes include, for example, antibodies, nucleic acids, receptors and their ligands.

The term "label" refers to a composition detectable by spectroscopic, photochemical, biochemical, immunochemical, or chemical means. For example, useful labels include $^{32}P$, fluorescent dyes, fluorescent proteins, electron-dense reagents, enzymes (e.g., as commonly used in an ELISA), biotin, dioxigenin, or haptens and proteins for which antisera or monoclonal antibodies are available. For example, polypeptides of this invention can be made detectable, by e.g., incorporating a radio-label into the polypeptide, and used to detect antibodies specifically reactive with the polypeptide. A label often generates a measurable signal, such as radioactivity, fluorescent light or enzyme activity, which can be used to quantitate the amount of bound label.

The term "nucleic acid probe" refers to a nucleic acid molecule that binds to a specific sequence or sub-sequence of another nucleic acid molecule. A probe is preferably a nucleic acid molecule that binds through complementary base pairing to the full sequence or to a sub-sequence of a target nucleic acid. It will be understood that probes may bind target sequences lacking complete complementarity with the probe sequence depending upon the stringency of the hybridization conditions. Probes are preferably directly labeled as with isotopes, chromophores, lumiphores, chromogens, fluorescent proteins, or indirectly labelled such as with biotin to which a streptavidin complex may later bind. By assaying for the presence or absence of the probe, one can detect the presence or absence of the select sequence or sub-sequence.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The terms "peptide" and "protein" refer to a polymer of amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "recombinant host cell" refers to a cell that comprises a recombinant nucleic acid molecule. Thus, for example, recombinant host cells can express genes that are not found within the native (non-recombinant) form of the cell.

The terms "isolated," "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein or nucleic acid molecule that is the predominant protein or nucleic acid species present in a preparation is substantially purified. Generally, an isolated protein or nucleic acid molecule will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies.

The term "immunoassay" refers to an assay that utilizes an antibody to specifically bind an analyte. The immunoassay is characterized by the use of specific binding properties of a particular antibody to isolate, target, and/or quantify the analyte.

The term "identical" in the context of two nucleic acid or polypeptide sequences refers to the residues in the two sequences that are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11–17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237–244 and Higgins and Sharp (1989) CABIOS 5: 151–153; Corpet, et al. (1988) Nucleic Acids Research 16, 10881–90; Huang, et al. (1992) Computer Applications in the Biosciences 8, 155–65, and Pearson, et al. (1994) Methods in Molecular Biology 24, 307–31. Alignment is also often performed by inspection and manual alignment. "Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "complementary" means that one nucleic acid molecule has the sequence of the binding partner of another nucleic acid molecule. Thus, the sequence 5'-ATGC-3' is complementary to the sequence 5'-GCAT-3'.

An amino acid sequence or a nucleotide sequence is "substantially identical" or "substantially similar" to a reference sequence if the amino acid sequence or nucleotide sequence has at least 80% sequence identity with the reference sequence over a given comparison window. Thus, substantially similar sequences include those having, for example, at least 85% sequence identity, at least 90% sequence identity, at least 95% sequence identity or at least 99% sequence identity. Two sequences that are identical to each other are, of course, also substantially identical.

A subject nucleotide sequence is "substantially complementary" to a reference nucleotide sequence if the complement of the subject nucleotide sequence is substantially identical to the reference nucleotide sequence.

The term "stringent conditions" refers to a temperature and ionic conditions used in nucleic acid hybridization. Stringent conditions are sequence dependent and are different under different environmental parameters. Generally, stringent conditions are selected to be about 5 to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

The term "allelic variants" refers to polymorphic forms of a gene at a particular genetic locus, as well as cDNAs derived from mRNA transcripts of the genes and the polypeptides encoded by them.

The term "fluorescence" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing," respectively) are particularly advantageous because the ratioing process provides an internal reference and cancels out variations in the absolute brightness of the excitation source, the sensitivity of the detector, and light scattering or quenching by the sample.

II. Lanthanide Binding Tags

The present invention provides a lanthanide binding tag (LBT) that is useful in one or more of the following applications: isolation and purification; fluorescence monitoring for isolation, purification, and assay development, magnetic phase contrast applications; and structural determination.

The LBT is a peptide that contains: (a) about 12 to about 30 amino acid residues, (b) at least two carboxylic groups and (c) at least one oxygen containing group selected from the group consisting of an backbone carbonyl group, the carboxyl terminus, Ser, Thr, Gln, Asn, or an oxygen of a bound solvent molecule.

Although not required, Ln ions can be sensitized by a neighboring chromophore (within 10 Å) of appropriate energy (Richardson, F. S. Chem. Rev. 1982, 82, 541–552) such as the amino acids tryptophan and tyrosine. Further, it is preferable to have an LBT which coordinates to the lanthanide ion via polydenate ligands which provide 6–12 (preferably 8 or 9) "hard" donor ligands including, in particular, the oxygens of the carboxylate and carboxamide ligands.

In one embodiment the LBT has a sequence:
$T^0$-$X^1$-$X^2$-$X^3$-$X^4$-$X^5$-$X^6$-$X^7$-$X^8$-$X^H$-$X^9$-$X^{10}$-$X^{11}$-$X^{12}$-$X^{13}$-$T^{14}$
where $T^0$ and $T^{14}$ are each independently absent or are an amino acid or peptide, $X^1$, $X^3$, and $X^5$ are each independently an amino acid with a metal binding side chain, $X^H$ is absent or is an amino acid or dipeptide, $X^2$, $X^4$, $X^6$, $X^8$, $X^7$, $X^9$, $X^{10}$, $X^{11}$, $X^{12}$, and $X^{13}$ are each independently an amino acid.

In one embodiment the LBT has a sequence:

$T^0$-$X^1$-$X^2$-$X^3$-$X^4$-$X^5$-$X^6$-$X^7$-$X^8$-$X^H$-$X^9$-$X^{10}$-$X^{11}$-$X^{12}$-$X^{13}$-$T^{14}$ where $T^0$ and $T^{14}$ are each independently absent or are an amino acid or peptide, $X^1$, $X^3$, and $X^5$ are each independently an amino acid with a metal binding side chain, $X^H$ is absent or is an amino acid or dipeptide, and $X^2$, $X^4$, $X^6$, $X^8$, $X^7$, $X^9$, $X^{10}$, $X^{11}$, $X^{12}$, and $X^{13}$ are each independently an amino acid, so long as at least one is an amino acid with a fluorophore-containing side chain (preferably Trp).

In another embodiment the LBT has a sequence:

$T^0$-$X^1$-$X^2$-$X^3$-$X^4$-$X^5$-$X^6$-$X^7$-$X^8$-$X^H$-$X^9$-$X^{10}$-$X^{11}$-$X^{12}$-$X^{13}$-$T^{14}$ where $T^0$ and $T^{14}$ are each independently absent or are an amino acid or peptide, $X^1$, $X^3$, and $X^5$ are each independently an amino acid with a metal binding side chain, $X^H$ is absent or is an amino acid or dipeptide, $X^2$, $X^4$, $X^6$, $X^8$, $X^9$, $X^{10}$, $X^{11}$, $X^{12}$, and $X^{13}$ are each independently an amino acid, and $X^7$ is an amino acid with a fluorophore-containing side chain (preferably Trp).

In another embodiment the lanthanide binding tag contains 14–30 amino acid residues and has a sequence:

$T^0$-$X^1$-$X^2$-$X^3$-$X^4$-$X^5$-Gly$^6$-Trp$^7$-$X^8$-$X^H$-Glu$^9$-$X^{10}$-$X^{11}$-Glu$^{12}$-Leu$^{13}$-$T^{14}$ where $T^0$ and $T^{14}$ are each independently absent, an amino acid or peptide;

$X^1$ is Asp, Asn, Ser, or Glu, $X^2$ is Trp, Tyr, Phe, Gln, Ile or Lys, $X^3$ is Asp, Asn, Ser, or Glu, $X^4$ is Trp, Tyr, Ala, Gln, Ile or Lys, $X^5$ is Asp, Asn, Ser, or Glu, $X^8$ is Trp, Tyr, Phe, Gln, Ile, Lys or Arg, $X^H$ is absent or is a glycine, $X^{10}$ is Trp, Tyr, Glu, Asp, Lys or Phe, and $X^{11}$ is Trp, Tyr, Glu, Asp, Lys or Leu.

Preferred lanthanide-binding peptides include:

Although not required, it is preferable that the LBT binds the lanthanide with a complete, closed shell coordination environment that does not enable adventitious binding by water.

When present, $X^0$ and $X^{14}$ preferably are amino acids or peptides containing 2–5 residues. Further, $X^0$ and $X^{14}$ can be cysteine containing peptides—which allows for the incorporation of a disulfide bridge in the LBT to preorganize the ligands. Preferably, the size of the loop formed by the disulfide bridge is 20 or less amino acids to preserve the advantage of a small motif. $X^0$ is preferably XXC, XCX, or XCXX, where X is any amino acid, preferably glycine or alanine. $X^{14}$ is CXX, XCX or XXCX, where X is any amino acid, preferably glycine or alanine. Preferably $X^0$ and $X^{14}$ are XCX and CXX, respectively or XCXX and XCX, respectively.

The disulfide constained LBT, ACA-DYNKDGWYEELE-CAA (known as CC2) binds to $Tb^{3+}$ with a $K_D$ of 300 nM, an order of magnitude more tightly than other reported Ca-binding peptides. (Kanellis, et al. *Arch. Biochem. Biophys.* 1983, 220, 530–540; Lopez, et al. *Proc. Natl. Acad. Sci. USA* 2002, 99, 1298–1303).

LBT peptides can be obtained using techniques known in the art, including solid phase peptide synthesis. Alternatively, LBT peptides can be obtained by expression of DNA encoding LBT peptides.

III. Fusion Peptides

The LBTs of the present invention can be used to create "fusion peptides." Fusion peptides can be generated by linking together the coding regions for the peptide of interest, or portion thereof, with a polynucleotide coding for a LBT. This generates a new, single coding region that gives rise to the fusion peptide.

The peptide of interest can be expressed in whole or in part. It may not be necessary to express an entire protein and, in some cases, it may be desirable to express a particular functional domain, for example, where the protein fragment remains functional but is more stable, or less antigenic, or both.

A variety of different peptides can be expressed according to the present invention, including both secreted and non-secreted peptides.

Suitable peptides that are normally secreted include soluble CD-4, Factor VIII, Factor IX, von Willebrand Factor, TPA, urokinase, hirudin, interferons, TNF,

```
Gly-Asp-Tyr-Asn-Lys-Asp-Gly-Trp-Tyr-Glu-Glu-Leu-Glu-Leu

Gly-Asp-Tyr-Asn-Lys-Asp-Gly-Trp-Tyr-Glu-Phe-Tyr-Glu-Leu

Gly-Asp-Phe-Asn-Gln-Asp-Gly-Trp-Ile-Glu-Glu-Leu-Glu-Leu

Gly-Asp-Phe-Asn-Lys-Asp-Gly-Trp-Ile-Glu-Phe-Tyr-Glu-Leu; and

Gly-Asp-Ile-Asn-Lys-Asp-Gly-Trp-Phe-Glu-Phe-Tyr-Glu-Leu.
```

The LBT binds a lanthanide ion with an affinity ($K_D$) of about 1 nM to about 10 μM, preferably 1–10 nM, most preferably 1–5 nM. Affinity is determined by titration with lanthanide and detection using fluorescence, circular dichroism, NMR or calorimetry. In the case of tightly binding sequences, it may be necessary to employ competition experiments.

The LBT binds any lanthanide, including $La^{3+}$, $Eu^{3+}$, $Sm^{3+}$, $Gd^{3+}$, $Ce^{3+}$, $Tb^{3+}$, $Dy^{3+}$, $Ho^{3+}$, $Er^{3+}$, $Pm^{3+}$, $Yb^{3+}$, or $Lu^{3+}$.

interleukins, hematopoietic growth factors, antibodies, albumin, leptin, transferin, peptide hormones and nerve growth factors.

Suitable peptides that are not normally secreted include cell surface receptors, transporters and channels such as GLUT2, CFTR, leptin receptor, sulfonylurea receptor, β-cell inward rectifying channels, protein processing enzymes such as PC2, PC3, and PAM, transcription factors such as IPF1, and metabolic enzymes and soluble enzymes found in the cytosol such as adenosine deaminase, phenylalanine hydroxylase, glucocerebrosidase.

IV. Genetic Constructs

The present invention also provides genetic constructs in the form of expression vectors and kits comprising an expression vector of the present invention. The expression vectors of the present invention are useful for creating fusion proteins comprising a lanthanide binding tag. Expression vectors for creating fusion proteins containing tags are well known in the art. Examples of tag-encoding vectors include the FLAG- or c-myc epitope-encoding pCMV-Tag vectors of Stratagene, the calmodulin-binding peptide (CBP)-encoding pCAL vectors of Stratagene, the polyhistidine-encoding pEF1/V5-His vectors of Invitrogen, and the in vivo biotinylation tag-encoding PINPOINT Xa vector of Promega. In light of the present disclosure, one of skill in the art will appreciate that essentially any vector containing another tag encoding sequence could instead, or in addition, be modified to encode a lanthanide binding tag of the present invention.

Expression vectors typically contain one or more promoters and may include one or more enhancer regions. Essentially any promoter or enhancer may be included in the expression vectors of the present invention as long as the promoter is capable of transcribing the open reading frame (ORF) of the lanthanide binding tag containing fusion protein. Types of promoters that may be used are those that are recognized by eukaryotic polymerases, prokaryotic polymerases, and viral (including phage) polymerases. The latter are particularly useful in in vitro transcription/translation methodologies. Furthermore, the promoter may be an inducible promoter. Of course, the expression vector may be designed to contain multiple promoters. Such vectors allow expression of the ORF in several different systems.

Generally, tag-encoding vectors contain a multiple cloning region (MCR). The MCR facilitates the creation of tag fusion proteins by providing a variety of restriction sites in which an ORF can be subcloned into the vector. When a fusion protein containing a tag at the amino terminus is desired, the MCR is downstream (relative to the promoter) of the lanthanide binding tag-encoding region. When a fusion protein containing a tag at the carboxyl terminus is desired, the MCR is upstream (relative to the promoter) of the lanthanide binding tag-encoding region.

The present invention also provides kits. Kits of the present may include one or more expression vectors of the present invention. For example, the kit may contain three vectors wherein the MCR is in a different reading frame in each vector. The kit may contain one or more vectors encoding a fusion protein. Such vectors may be useful as positive controls and for utilities in which the user wishes to use a particular fusion protein rather than create a vector containing a protein of the user's choice.

The kits also may include accessory components. Accessory components of the present invention that may be included in a kit include components for purifying the expressed protein, competent cells, one or more proteases, antibodies, and instructions directing the user on how to use the kit. One or more of the accessory components may be included in a kit with the expression vector or may provided in its own kit.

Examples of components for purifying the expressed protein include columns, resins, or beads having affinity for the expressed protein. For example, for purifying proteins with polyhistidine tags, Sepharose resins containing $Ni^{2+}$ or $Co^{2+}$ are typically included in kits. When fusion proteins containing a polyhistidine tag are added to a $Ni^{2+}$ or $Co^{2+}$ Sepharose column, the polyhistidine tags bind the immobilized media while other proteins are eluted off. The purified polyhistidine tag-containing protein then may be eluted off the column with competing imidazole or at acidic pH. Similarly, kits of the present invention may contain columns, resins, or beads containing one or more lanthanides. Furthermore, the kit may contain solutions for washing and eluting the lanthanide binding tag-containing protein from the resin or bead. The elution solution may contain a protease than cleaves a protease susceptible site within the expressed protein.

V. Antibodies

Fusion peptides may be useful in producing secreted forms of proteins that are not normally secreted or producing molecules that are immunologically tagged. Tagged proteins may be more easily purified or monitored using antibodies to the tag.

VI. Purification

Crystals can be made after purifying the LBT fusion peptides that are obtained by expression in cell culture as described above.

The LBT fusion peptide is purified to homogeneity. Purity of the LBT fusion peptide is measured with sodium dodecyl sulfate polyacrylamide gel electrophoresis (SDS-PAGE), mass spectrometry (MS) and high performance liquid chromatography (HPLC). If the LBT fusion peptide is to be crystallized, it should be preferably at least about 90% pure, preferably at least about 95.0% pure, more preferably at least about 99.0% pure. Fusion peptides may be crystallized at lower purity. Initial purification of the LBT fusion peptide can be carried out by conventional techniques, such as hydrophobic interaction chromatography, ion exchange chromatography, affinity chromatography or size exclusion chromatography.

VII. Use of LBTs in Fluorometric Applications

The present invention also provides methods for using LBTs in fluorometric applications. In one embodiment, the fluorescence of fusion peptides containing the LBTs can be used to quantitate the fusion peptide itself or quantitate the binding of the fusion peptide to a protein by observing the decrease in fluorescence when peptide which does not contain the LBT is added.

Lanthanide chelates have important photophysical properties that render them amenable to technological applications. For example, chelates of $Eu^{3+}$ and $Tb^{3+}$ in particular have been used as luminescent probes. Since the ligand field has very little effect on the well-shielded f orbitals, the f—f transitions of Ln ions result in characteristic and sharp emission bands. As a consequence of the Laporte forbidden f—f transitions, Ln ions are weak absorbers. However, indirect excitation is possible via energy transfer from a sensitizing chromophore with an excited triplet state of appropriate energy. The $^5D_0$ to $^7F_1$ and $^5D_4$ to $^7Fj$ transitions back to the ground state are also forbidden, thereby giving rise to long-lived fluorescence emissions. This property is ideal behavior for time-resolved fluorometry. The emission spectrum can be measured after an appropriate time delay, thus allowing the organic background fluorescence from biological components to decay before the long-lived emission spectrum of the Ln is measured, greatly increasing the sensitivity of the method. An additional advantage of Ln ions is their large Stokes shift, which allows the excitation and emission wavelengths to be well separated and therefore eliminate interference form the intense excitation source. Further, lanthanide chelates demonstrate millisecond luminescence lifetimes, a property that is ideal for time-resolved fluorometry. (Gudgin Dickson & Diamandis, *Pharmac. Ther.* 1995, 66, 207–235; Johnstone & Turner, Ed.; Oxford Univ: New York, 1997; Vol. 1, pp 193–214). These properties of the Ln chelates allow the LBT sequences with bound lanthanide ions to be useful as intrinsic protein fluorophores for monitoring proteins by fluorescence (steady state or lifetime measurements) or in fluorescence resonance energy transfer (FRET) studies.

Applications such as quantitation of protein expression and the rapid and simultaneous assessment of the co-expression of a number of gene products in a biochemical pathway can be envisioned. For example, if expression products are visualized using 1D or 2D gel electrophoresis together with luminescence enhanced photography this process would only reveal the tagged proteins in gel electrophoresis. Additionally, direct analyses of protein/protein interactions and the study of ligands that might interfere with them could be directly probed without the intermediacy of indirect steps that are necessary in the DELFIA (dissociation-enhanced lanthanide fluoroimmunoassay) system. It will also be possible to use the lanthanide chelate as the acceptor in FRET-based experiments to measure both static distances and time-dependent variation of discrete distances in biological systems. The LBTs represent alternatives for radioisotope labeling, as well as substitutes for standard organic fluorescent dyes that may be susceptible to photobleaching. While detection limits of many lanthanide complexes are remarkable ($10^{-9}$–$10^{-12}$ M), a major current limitation of lanthanide-based probes is that the best characterized lanthanide complexes are built upon synthetic chelating ligands that must be attached to a protein through chemical modification. This mode of protein incorporation greatly limits potential applications and furthermore deters all but the most adept at the "chemistry" of protein derivatization from applying the lanthanide chelates as tools. In addition, with regard to direct protein binding, while certain native peptide sequences do show some affinity for lanthanide ions, there is to date no systematic way to specifically introduce a peptide sequence into an expressed protein to engineer desirable photophysical properties (based on lanthanide complexes) into the construct.

The LBTs of the present invention can be used to detect proteins. The LBTs can be used to quantitatively evaluate the co-expression of a family of proteins in a metabolic pathway when used together with 1D or 2D gel electrophoresis and luminescence enhanced photography (see Hill et al., *Anal. Biochem.* 1994, 216:439–443). One advantage of using the LBT-based system are that the tag can be observed and quantified directly in solution by fluorescence in the presence of added terbium or in an SDS-PAGE gel without the need for further manipulation including transfer to nitrocellulose and western blot analysis. Additionally, a major advantage of using the LBT results from the unique long lifetime (high μs-ms) of the lanthanide in the Ln-LBT complex which allows complete elimination of background signals due to fluorescent organic components which are short lived (ns). Currently, the limit of detection is 10 ng protein for $Tb^{3+}$ bound to the non-optimized lanthanide binding sequence of oncomodulin in an SDS-PAGE gel (Hill et al. *Anal. Biochem.* 1994, 216, 439–443). With the CC2 peptide described in section C, we have now improved fluorescence by a factor of 15, bringing the limit of detection into the high pg range. This makes the LBT detection method superior in sensitivity to both Coomassie (1 μg) and silver staining (2–5 ng). The protein-LBT conjugates of the present invention should be directly observable in the low pg range. While such limits of detection may be modest in terms of available technologies such as mass spectroscopy or analysis of epitope-tagged proteins, it should be stressed that the encoded LBT would provide direct and quantitative information. Such photophysical monitoring techniques will be of exceptional value when dealing with products of ORFs of unknown biological function, as is the case in proteomics, and will be possible with the natively expressed LBTs.

The LBTs of the present invention can also be used to assay for protein/protein and protein/peptide interactions and the study of ligands that might interfere with these interactions. To date a significant number of assays, based upon GFP-labeled proteins, where the fluorescence of one or two GFP conjugates have been developed (e.g., Kraynov et al., *Science,* 2000, 290:333–337; Mitra et al., *Gene,* 1996, 173:13; Park et al., *Protein Sci.,* 1997, 6:2344–49.) The LBT conjugates of the present invention can be used as alternative to Green Fluorescence Protein (GFP) adducts for in vitro analyses of protein/protein interactions. For example, the LBTs of the present invention can be used to monitor the interaction between Ras and a short peptide derived from the sequence of Raf, a protein kinase regulated by Ras binding. A fusion peptide of a LBT and a Raf-derived peptide can be used monitor their interaction with Ras. Ras proteins were discovered as products of mutant ras genes that promote cancer by interfering with intracellular pathways controlling cell proliferation and differentiation.

VIII. Use of LBTs in Crystallographic Applications

Once a LBT fusion peptide is obtained, it can be crystallized and analyzed to determine its three dimensional structure. It is useful to know the structure of a polypeptide because it provides information regarding: the active site of the polypeptide as well as the surface properties of the polypeptide. After the three dimensional structure is determined for the LBT fusion peptides with the lanthanide bound, the three dimensional structure can be used in computational methods to design a synthetic ligand for the LBT fusion peptides and further structure/activity relationships can be determined through routine testing using the assays described herein and known in the art.

In general, a crystal is useful for x-ray crystallography if it exhibits discrete maxima of spots at specific intervals (i.e., positions on the x-ray detector defined by Bragg's Law ($n\lambda = 2d \sin \theta$) and the unit cell parameters of the crystal) and the crystal diffraction pattern exhibits a minimum Bragg spacing of $d \leq 3$ Å. A general discussion of Bragg's Law and the unit cell parameters of a crystal is found in Halliday and Resnick, *Fundamentals of Physics,* 2nd Ed. (John Wiley and Sons, Inc., 1981).

General methods for the preparation and analysis of peptide crystals have been disclosed. See Alexander McPherson, *Preparation and Analysis of Protein Crystals* (Kreiger Publishing, 1989). Briefly, a LBT fusion peptide is equilibrated with a saturating concentration of lanthanide at a temperature that preserves the integrity of the fusion peptide; usually from about 2 to 37° C., preferably from about 2 to 20° C.

Thereafter, crystal formation is encouraged by bringing the solution to supersaturation in a controlled manner. See Jan Drenth, *Principles of Protein X-Ray Crystallography* (Springer-Verlag, 1994). Regulated temperature control is desirable to improve crystal stability and quality. Temperatures from about 4 to 25° C.—are used during crystal formation, depending on that temperature which is optimal for protein stability over the period of crystal growth (typically 3–10 days).

The typical method of determining the three-dimensional structure from the diffraction pattern in x-ray crystallography typically involves multi-wavelength anomalous diffraction (MAD) or multiple isomorphous replacement (MIR)

analysis. The x-rays used typically have wavelengths between about 0.9 to 1.7 Å. The x-rays are typically produced by synchrotron radiation or with a copper anode X-ray generator.

Binding of a heavy atom to the polypeptide is required for both MAD and MIR phase determination. High-throughput heavy atom derivatization is necessitated by the demands of the structural genomics initiative. There are 100,000 protein-coding genes expected in the human genome. Protein modelers estimate that about 10,000 representative protein structures are necessary to cover not only all expected folds but also sequence variation between the fold families. Thus, it is anticipated that those protein structures that are not determined experimentally will be predicted by computational modeling. Overall, the project has the potential to produce up to 50,000 new structures at a maximum total cost of $5 billion dollars. The steps involved in achieving this output include (1) expression and purification of protein material from open reading frames (ORFs), (2) crystal growth, (3) collecting data and solving the phases, and (4) structure analysis. Within the structure solution step (3) lies the problem of how to derivative and solve phases for proteins in an automated fashion.

In the past, heavy atom derivatization was approached empirically, by soaking crystals in solutions of heavy metals such as Hg, Pt, Au and Ur. Comparison with the native, unsoaked data set determines the extent and nature of derivatization. However, this multiple isomorphous replacement (MIR) method is unreliable and necessitates the collection of multiple data sets to achieve success. The presence of heavy metals often disturbs the crystal lattice, destroying diffraction and introducing non-isomorphism (differences in unit-cell lengths and angles). Recently, the more reliable method of selenomethionine (SeMet) labeling of proteins has been embraced. The protein is expressed in a bacterial strain auxotrophic for methionine and grown on minimal media plus SeMet. Thus, SeMet is incorporated at the level of protein expression in place of methionine in a reliable and quantitative fashion. The use of SeMet labeling in conjunction with multiwavelength anomalous dispersion (MAD) phasing has revolutionized structure determination via X-ray crystallography with over 40 structures solved by this method from the time that the method was introduced in 1995. However, there are drawbacks to SeMet labeling which may limit its usefulness in high throughput structure solution efforts including; (1) Derivatization occurs only at Met residues in the target protein, thus the number of sites is controlled solely by the primary sequence of the protein; (2) The phasing power is only 8/3 times that of the typical light atoms that constitute proteins (C, O, N, S), necessitating that at least one SeMet be present for every 100 amino acids, and (3) SeMet is deleterious to bacterial growth, lowering cell yield and thus protein production.

Although the success of the SeMet method are numerous, the drawbacks cited are serious enough for researchers to explore other options. For instance, the use of the naturally occurring sulfur for MAD phasing has been considered as an alternative strategy. The structure of the light-emitting protein obelin was recently solved to 1.7 Å resolution by this method. This was the second structure that was reported solved by this method. However, since the number of anomalously scattering electrons is so small for S (16 electrons), the anomalous signal is low, requiring that the crystal diffract very strongly in order to collect accurate enough data for phasing. Also, since this method still does not free the researcher from the constraints of the target primary sequence, the only difficulty ameliorated is the necessity of introducing the heavy atom scatterer.

Applications of LBTs in macromolecular crystallography arise since lanthanides interact with X-ray light to produce scattering and anomalous scattering. The magnitude of scattering for lanthanides is 5.8 times greater than that of the typical light atoms that constitute proteins (C, O, N, S), and absorption edges for anomalous scattering of lanthanides with absorption edges in the conveniently accessible central region include $Gd^{3+}$, $Tb^{3+}$, $Dy^{3+}$, $Ho^{3+}$. In macromolecular X-ray crystallography the LBTs would provide rapid and efficient preparation of heavy-atom derivatives for structure determination. Structure determination could be approached by MIR, MAD, single-wavelength anomalous scattering (SAD), or single-isomorphous replacement (SIR) using the LBT with bound lanthanide. A single lanthanide can provide enough power to phase an 80 kDa protein. The LBTs would allow control over the number and location (N-and/or C-terminus) of heavy-metal sites on the target protein. Thus, derivatization would be freed from empirical searches (as in the MIR method) and constraints of the primary sequence (as in SeMet labeling and S MAD). Tagged proteins should be amenable to crystallization because the stability of the LBT fold and high affinity of the lanthanides (low nM $K_D$) should prevent interferences of the LBT with folding of the target protein or competition with metals important for target protein stability and/or activity. Effectively the LBT would enable high throughput heavy atom derivatization and therefore accelerate the structure determination process by eliminating further screening for heavy atom derivatives. The LBT-compatible crystallization matrix can be utilized to obtain new crystallization conditions for LBT-protein conjugates in the presence of $Tb^{3+}$. In addition, the presence of the LBT does not interfere with the formation of crystals that diffract to atomic resolution.

IX. Use of LBTs in Magnetic Imaging Applications

Ln ions, bound either to native $Ca^{2+}$-binding sites or to adventitious sites in proteins, have been used as magnetic probes for NMR structural analysis. Similarly here, the LBTs of the present invention can be bound to Ln ions and used as magnetic probes. Opella and coworkers have extended this idea by co-expressing membrane proteins with a Ca-binding loop sequence (e.g. J. Am. Chem. Soc., 2000, 122:11733–34; J. Mag. Res., 2000, 146:381–4). Ln ions coordinated in this added site were used to align the membrane protein in micelles for NMR spectroscopy.

Ln ions are known to be useful in contrasting agents for magnetic resonance imaging. Often it is preferable to direct the contrasting agent to a particular tissue or region of the patient's body, e.g., blood vessel, heart, liver, kidney, or tumor. For a review of targeting contrasting agents, see Gupta and Weissleder, "Targeted contrast agents in MR imaging," *Magn. Reson. Imaging Clin. N. Am.* 4(1):171–184, 1996. To direct the contrasting agent, often it is associated with an antibody, peptide, protein, polysaccharide, polymer, liposome, or cell that locates to a specific region or tissue or binds to one or more cells within the region or tissue.

Gadolinium (Gd) is commonly used as a contrasting agent. Methods of directing Gd to a particular tissue are known in the art (Anderson et al., "Magnetic resonance contrast enhancement of neovasculature with alpha(v)beta (3)-targeted nanoparticles," *Magn Reson Med* 44(3):433–9, 2000; Aime et al., "Non-covalent conjugates between cationic polyamino acids and GdIII chelates: a route for seeking accumulation of MRI-contrast agents at tumor targeting sites," *Chemistry* 6(14):2609–17, 2000; Opsahl et al., "Tumor imaging with a macromolecular paramagnetic contrast agent: gadopentetate dimeglumine-polylysine," *Acad*

*Radiol* 2(9):762–7, 1995). In Anderson et al., Gd-perfluorocarbon nanoparticles were linked to alpha(v) beta(3) integrin antibody DM101. Because this particular integrin is known to be expressed on the endothelial cells of the neovasculature, the Gd conjugate was effective in improving MRI imaging of angiogenic vessels. In Opsahl et al., Gd was directed to a tumor in the form of gadopentetate dimeglumine-polylysine. Tumor cells tend to have a higher affinity for positively charged amino acids like lysine than their non-tumor counterparts (Aime et al., 2000).

The Ln binding tags of the present invention may be used in conjugates for improving MRI imaging. The Ln binding tags may be conjugated to an antibody, antibody fragment, peptide, protein, polysaccharide, polymer, liposome, or cell. When the conjugate comprises a polypeptide, the conjugate may be in the form of a fusion protein. The conjugate comprising the Ln binding tag may include a compound that binds a particular cell, tissue or region within the patient. Alternatively, the conjugate may include a compound that binds to a compound that binds to a particular cell, tissue or region. For example, a biotinylated antibody specific for a tumor cell may be administered to a patient followed by administration of a streptavidin/Ln binding tag fusion protein. The Ln binding tag is complexed with a lanthanide ion prior to administration to the patient.

When administration to a patient is desired, it is preferred that the Ln binding tag conjugate be placed in a composition comprising a pharmaceutical excipient or a sterile buffer or solution, such as water, saline, Ringer's solutions, dextrose solution, or 5% human serum albumin. Liposomes and non-aqueous vehicles such as fixed oils may also be used. Furthermore, administration may be by essentially any means as long as the administration allows for the conjugate to reach the cell, tissue, or region in the patient to be subjected to MRI. Such administration routes include orally, nasally, topically, intravenously, interperitoneally, vaginally, intradermally, transdermally, transmucosally, rectally, and intertumorally.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, for example, parabens, chlorobutanol, phenol, ascorbic acid, and thimerosal, can contain microorganism contamination. Isotonic agents, for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the Ln tag containing conjugate in the required amount in an appropriate solvent with one or a combination of ingredients as required. Generally, dispersions are prepared by incorporating the Ln tag containing conjugate into a sterile vehicle that contains a basic dispersion medium, and the other required ingredients.

Oral compositions generally include an inert diluent or an edible carrier. They can be enclosed in gelatin capsules or compressed into tablets. For the purpose of oral administration, the Ln tag containing conjugate can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compositions are delivered as an aerosol spray from a nebulizer or a pressurized container that contains a suitable propellant, e.g., a gas such as carbon dioxide.

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

X. EXAMPLES

Example 1

LBT-Ubiquitin

The small monomeric pyotein ubiquitin was chosen as the first protein to co-express with an LBT, LBT1 (GDYNKDGWYEELEL). This system was used to pilot preliminary X-ray crystallographic studies and additionally for the development of useful methods to quantify protein expression levels utilizing the luminescent properties of the Tb-bound tag. The optimum N-terminal LBT-tagged protein construct also included a $His_6$-purification tag directly upstream of the LBT sequence (FIG. 1). Additionally, the stop sequence (Gly-Pro) for DAPase, an exodipeptidase is engineered into the start of the LBT sequence to enable removal of the $His_6$-tag using the Tagzyme protocol (Qiagen). Other strategies including factor Xa or enterokinase protease sites between the HIS-tag and the LBT (for tag removal) proved inferior to the Tagzyme approach due to non-specific cleavage at different sites within the engineered tags. The $His_6$-LBT-Ubiquitin (HIS-LBT-Ub) was expressed in BL21 PlysS E. coli cells. The protein was purified by $Ni^{2+}$ affinity chromatography under native conditions and characterized by SDS PAGE gel analysis.

The HIS-LBT-Ub identity was confirmed by mass spectroscopy (ES-MS). In general, expression levels are excellent (>15 mg/L) and the protein conjugates are well behaved with good solubility and stability properties. The $His_6$-tag of the HIS-LBT-Ub protein was also cleanly removed using the Tagzyme protocol. Most importantly the presence of the LBT tag does not interfere with implementation of the HIS-tag purification strategy.

Figure 2:
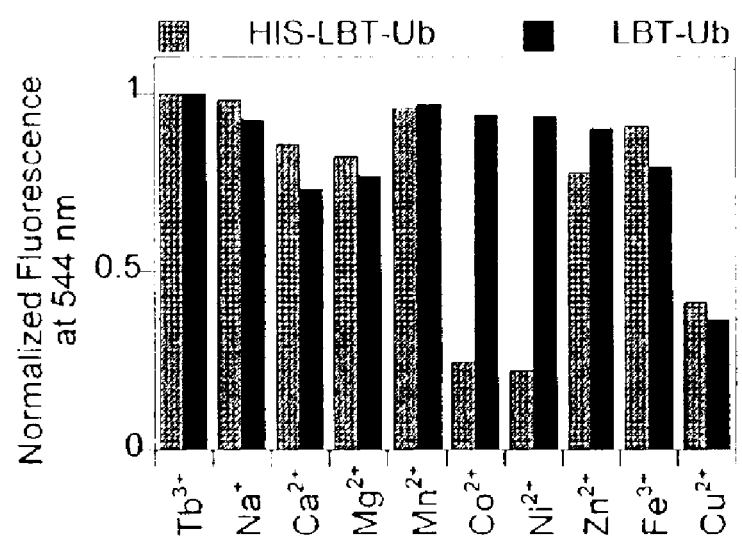
FIG. 2 is a graph showing the competition analysis of Tb-loaded HIS-LBT-Ub in the presence of competing metal cations (5 mM $Na^+$, $Ca^{2+}$, $Mg^{2+}$ and 5 µM $Mn^{2+}$, $Co^{2+}$, $Ni^{2+}$, $Cu^{2+}$, $Zn^{2+}$, $Fe^{3+}$). The competing ion was added to the LBT-conjugate (5 µM) with 10 µM $Tb^{3+}$ in 10 mM HEPES buffer pH 7 ($\lambda_{ex}$=285 nm).

The purified LBT-protein conjugates were further studied to assess whether the fluorescence and binding properties of the LBT were preserved in the protein conjugates. Fluorescence spectroscopy of a 10 µM solution of HIS-LBT-Ub upon addition of $Tb^{3+}$ shows comparable properties to the isolated LBT peptide with fluorescence at 350 nm quenched upon titration with $Tb^{3+}$, and appearance of the characteristic Ln-based bands at 490 and 545 nm. The intensity of the lanthanide bands demonstrates that appending a HIS-tag as well as the ubiquitin protein to the LBT sequence has not affected the fluorescence behavior of the LBT. Binding studies also reveal that integration into a protein construct does not affect the affinity of the LBT for lanthanide ions; the $K_D$ values of the free LBT and the HIS-LBT-Ub were both determined to be 5 µM using calorimetry. Metal ion competition analysis of the new protein conjugates also shows that the LBT-Ub continues to demonstrate good $Tb^{3+}$ selectivity even when appended to a native protein (FIG. 2). Interestingly, competition analysis of the HIS-LBT-Ub conjugate shows more interference with Ln binding in the presence of $Co^{2+}$, $Ni^{2+}$, and $Cu^{2+}$, presumably due to the binding of these ions to the contiguous $His_6$ site.

The preliminary studies indicated that even the small protein ubiquitin tolerates attachment of the LBT and that the LBT does not appear to interfere with expression efficiency, protein stability or purification using a HIS-tag. Importantly the photophysical and thermodynamic properties of the LBT-protein conjugate appear to be independent of the presence of the ubiquitin supporting the hypothesis that the LBT will be a convenient, non-invasive tag of minimal dimensions.

Example 2

LBT-Protein Conjugate Crystallization

It is desirable to obtain crystals of LBT-protein conjugates from conditions that are compatible with lanthanide binding to the LBT. Although lanthanide ions bind to the LBT with high nM to low µM affinity, certain crystallization agents, when used at the molar concentrations typical for crystallography, can compete with the LBT for lanthanide binding. An LBT-compatible sparse matrix crystallization screen that excludes those agents that are incompatible with the LBT and replaces them with LBT compatible agents was developed. The ability of this newly developed screen to uncover crystallization conditions for a representative variety of LBT-protein conjugates will be established. Toward this goal the fluorescence of the HIS-LBT-Ub protein in the presence of $Tb^{3+}$ and a number of polymers, counterions, and other additives were used to establish the compatibility of the LBT tag with common protein crystallization agents.

Figure 3:
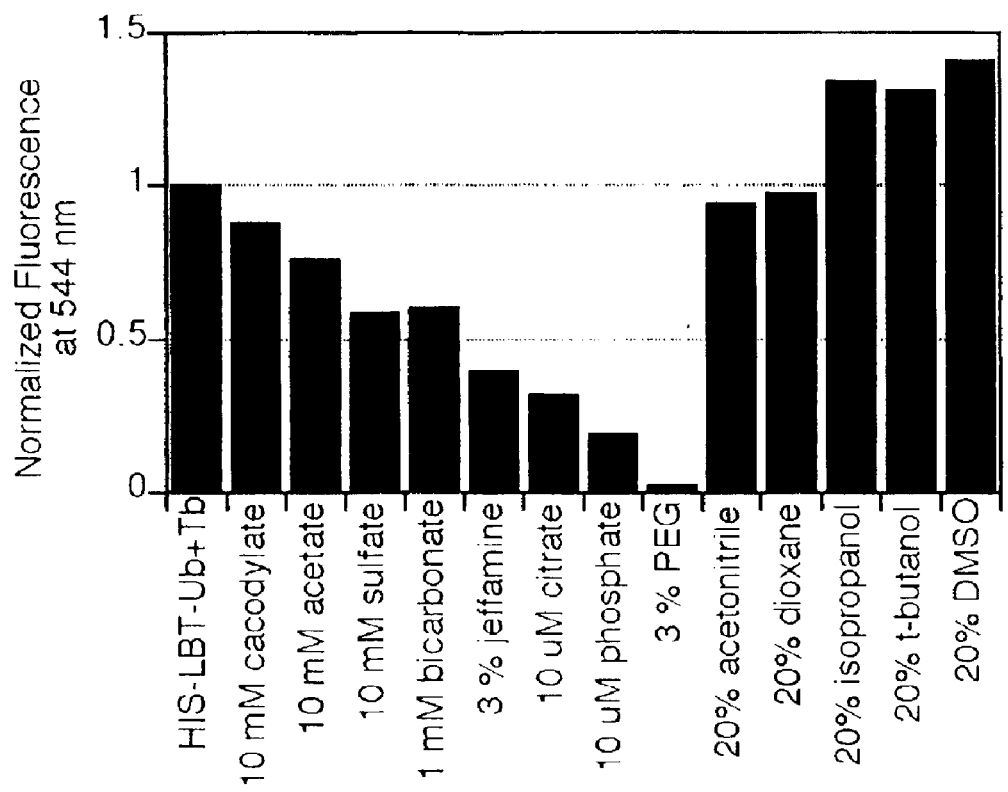
FIG. 3 is a graph comparing the standardized emission maxima at 544 nm of 10 µM HIS-LBT-Ub protein with 10 µM $Tb^{3+}$ and various additives.

As illustrated in FIG. 3, the fluorescence of the Tb-bound HIS-LBT-Ub is strong (>60% of the control fluorescence) in the presence of a number of common organic and inorganic additives (acetate, sulfate, cacodylate, bicarbonate, and several organic solvents). Phosphate, citrate, jeffamine, and polyethylene glycol are detrimental to the luminescence of HIS-LBT-Ub indicating that they may interfere with Ln binding. These data clearly establish the reagents compatible with LBTs for use in sparse matrix protein crystallization screens with LBT1. In the future, new generation LBT designs may further expand the scope of useful additives.

The most widely used sparse crystallization matrix for finding crystallization conditions for macromolecules of unknown structure is that delineated by Jancarik and Kim (*J. Appl. Cryst.* 1991, 24, 409–411). The conditions comprising this screen were further tested for LBT compatibility by setting up crystals as is typical for a new protein and checking the droplets for fluorescence (hence terbium binding). A solution of HIS-LBT-Ub (26 mg/ml) dissolved in 1 mM HEPES, pH 7.4 buffer, 0.3 M NaCl, 1 mM $CaCl_2$ and 6.0 mM $TbCl_3$ was set up using hanging-drop geometry. Equal volumes (2 µl) of protein solution and well solution were used. Before sealing the wells, each droplet was observed under a hand-held UV lamp (short-wavelength setting) for fluorescence. This rapid screening method provided results consistent with those determined in solution. Together with the fluorescence measurements on selected agents detailed above, these experiments have now defined those conditions compatible with Ln binding to LBT-protein conjugates. These conditions will be used in the development of an LBT-compatible sparse matrix screen.

Crystals of the HIS-LBT-Ub construct in the presence of 1 equivalent $TbCl_3$ were optimized from conditions found using the LBT-compatible crystallization matrix (described below).

Figure 4:
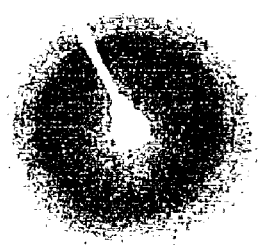
FIG. 4 shows the diffraction pattern of a HIS-LBT-Ub crystal. Note that the edge of the plate is at 2 Å.

The optimized crystals, grown from 2.0 M ammonium sulfate, 0.1 M sodium acetate, are approximately 0.3 mm per side and diffract to better than 2.7 Å resolution on an Rigaku RU300 rotating anode X-ray generator. A single 1 oscillation is depicted in FIG. 4. The crystals grow in space group $P3_121$ with unit cell-dimensions a=57.8 Å, b=57.8 Å, and c=130.2 Å. It is of note that this crystal form has not been reported previously in the literature. It is also noteworthy that ubiquitin has been found to be difficult to crystallize in the past due to very high solubility and that the LBT is relatively large compared with the protein itself (15 vs 76 amino acid residues) yet crystallization has still been achieved. Therefore, this result demonstrates that the presence of the LBT does not appear to inhibit crystallization, even in a relatively challenging system.

These results also demonstrate that the LBT-compatible crystallization matrix can be utilized to obtain new crystallization conditions for LBT-protein conjugates in the presence of $Tb^{3+}$. In addition, the presence of the LBT does not interfere with the formation of crystals that diffract to atomic resolution. Single wavelength and multi-wavelength data sets will now be obtained on the HIS-LBT-Ub crystals in order to solve the structure of the LBT-protein conjugate via molecular replacement and MAD phasing using the Tb anomalous signal.

Example 3

Binding of LN to Crystalline LBT-Protein Conjugates

The presence of bound terbium is indicated by the fluorescence of the LBT-protein conjugates in the solution state.

In addition, the presence of bound Ln produces X-ray fluorescence of LBT-protein conjugates in the crystalline state. Both the HIS-LBT-Ub construct and the reconstituted RNAse-LBT-S-peptide were subjected to crystallization trials in the presence of the $TbCl_3$. Initial crystallization conditions were obtained using HIS-LBT-Ub at 26 mg/ml or RNAse-LBT-S-peptide (1:1 RNAse:LBT-S-peptide, total protein concentration 20 mg/mL) and 3.0 mM $TbCl_3$ with the LBT-compatible sparse matrix screen conditions described above. Refinement of initial hits is now underway. Small crystals (<0.1 mm per side) of RNAse-LBT-S-peptide were grown from 0.2 M ammonium sulfate, pH 4.0, 28% PEG 4000. The crystals were washed in Paratone-N before insertion in the beam to act as a cryoprotectant and to remove any unbound lanthanide. Although these crystals are not yet of sufficient size to collect diffraction data, X-ray fluorescence measurements made at the $Tb^{3+}$ $L_{III}$ edge (7.514 keV) (beamline X4a, Brookhaven National Laboratories) showed a significant absorption signal. Therefore, while the initial conditions included PEG as a precipitant, it appears that these crystallization conditions produce LBT-protein with $Tb^{3+}$ bound. Optimization of crystallization can be done using methods known in the art. Once the S-protein/LBT-S-peptide and HIS-LBT-Ub crystallization conditions are optimized, the bound Ln will be used to provide de novo phases for these proteins via MAD phasing.

Example 4

Development of an LBT-Compatible Screen

Sparse matrix screening allows effective and rapid identification of crystallization conditions for macromolecules. (Jancarik & Kim, *J. Appl. Cryst.* 1991, 24, 409–411; Carter et al., *J. Biol. Chem.* 1979, 254, 12219–12223). In this method the large number of possible crystallization variables is represented by a very coarse matrix of crystallization conditions (pH, ionic strength, additives, and precipitants). The results of initial screens are analyzed to build finer grids around selected conditions. The sparse matrix screen method has become the most popular method of obtaining crystals of macromolecules not previously crystallized. The screen proposed by Jancarik and Kim, which comprises 50 conditions, is commonly used in conjunction with the novel precipitant screen (Cudney, et al., *Acta Cryst.* 1994, D50, 414–423) comprised of an additional 48 conditions containing organic precipitants such as Jeffamine, dioxane, t-butanol, and 1,6-hexanediol.

The LBT-compatible screen is derived from these two screens. The conditions containing precipitants identified via solution screens as competitive with lanthanide binding were removed (phosphate and polyethylene glycol). Conditions containing citrate buffer are replaced by acetate buffer (citrate inhibits Ln binding) and conditions containing polyethylene glycol are replaced by the non-volatile precipitant 2-methyl-2,4-pentanediol (MPD) for polyethylene glycol. Thus the final LBT-compatible matrix contains a total of 72 conditions (3×24-well trays; See Table 1).

TABLE 1

LBT-Compatible Matrix 1  30% MPD, 0.1 M Na Acetate pH 4.6, 0.02 M Calcium Chloride
2  0.4 M K, Na Tartrate
3  2.0 M Ammonium Sulfate, 0.1 M Tris HCl pH 8.5
4  30% MPD, 0.1 M Na Hepes pH 7.5, 0.2 M Sodium Acetate
5  30% MPD, 0.1 M Tris HCl pH 8.5, 0.2 M Magnesium Chloride
6  1.4 M Sodium Acetate, 0.1 M Na Cacodylate pH 6.5
7  30% iso-Propanol, 0.1 M Na Cacodylate pH 6.5, 0.2 M Sodium Acetate
8  30% MPD, 0.1 M Na Acetate pH 5.6, 0.2 M Ammonium Acetate
9  30% MPD, 0.1 M Na Acetate pH 4.6, 0.2 M Ammonium Acetate
10  30% iso-Propanol, 0.1 M Na Hepes pH 7.5, 0.2 M Magnesium Chloride
11  30% MPD, 0.1 M Tris HCl pH 8.5, 0.2 M Sodium Acetate
12  28% MPD, 0.1 M Na Hepes pH 7.5, 0.2 M Calcium Chloride
13  30% MPD, 0.1 M Na Cacodylate pH 6.5, 0.2 M Ammonium Sulfate
14  1.5 M Lithium Sulfate, 0.1 M Na Hepes pH 7.5
15  30% MPD, 0.1 M Tris HCl pH 8.5, 0.2 M Lithium Sulfate
16  30% iso-Propanol, 0.1 M Tris HCl pH 8.5, 0.2 M Ammonium Acetate
17  25% MPD, 0.1 M Na Acetate pH 4.6, 0.2 M Ammonium Sulfate
18  30% MPD, 0.1 M Na Cacodylate pH 6.5, 0.2 M Magnesium Acetate
19  30% MPD, 0.1 M Tris HCl pH 8.5, 0.2 M Sodium Acetate
20  30% MPD, 0.1 M Na Hepes pH 7.5, 0.2 M Magnesium Chloride
21  20% iso-Propanol, 0.1 M Na Acetate pH 4.6, 0.2 M Calcium Chloride
22  1.0 M Sodium Acetate, 0.1 M Iimidazole pH 6.5
23  20% iso-Propanol, 0.1 M Na Hepes pH 7.5, 0.2 M Sodium Acetate
24  30% MPD, 0.1 M Na Cacodylate pH 6.5, 0.2 M Sodium Acetate
25  0.8 M K, Na Tartrate, 0.1 M Na Hepes pH 7.5
26  30% MPD, 0.2 M Ammonium Sulfate
27  2.0 M Ammonium Sulfate
28  4.0 M Sodium Formate
29  2.0 M Sodium Formate, 0.1 M Na Acetate pH 4.6
30  8% MPD, 0.1 M Tris HCl pH 8.5
31  8% MPD, 0.1 M Na Acetate pH 4.6
32  1.4 M Sodium Acetate, 0.1 M Na Hepes pH 7.5
33  2% MPD, 0.1 M Na Hepes pH 7.5, 2.0 M Ammonium Sulfate
34  20% iso-Propanol, 0.1 M Na Acetate pH 5.6, 20% MPD
35  10% iso-Propanol, 0.1 M Na Hepes pH 7.5, 20% MPD
36  30% MPD
37  0.2 M Magnesium Formate
38  18% MPD, 0.1 M Na Cacodylate pH 6.5, 0.2 M Zinc Acetate
39  18% MPD, 0.1 M Na Cacodylate pH 6.5, 0.2 M Calcium Acetate
40  2.0 M Ammonium Sulfate, 0.1 M Sodium Acetate pH 4.6
41  2.0 M Ammonium Phosphate, 0.1 M Tris HCl pH 8.5
42  2% MPD, 1.0 M Lithium Sulfate
43  15% MPD, 0.5 M Lithium Sulfate
44  10% MPD, 2.0 M Sodium Chloride
45  0.5 M Sodium Chloride, 0.01 M CTAB, 0.01 M Magnesium Chloride
46  35% Dioxane
47  5% iso-Propanol, 2.0 M Ammonium Sulfate
48  1.0 M Imidazole pH 7.0
49  10% Ethanol, 1.5 M Sodium Chloride
50  2.0 M Sodium Chloride, 0.1 M Na Acetate pH 4.6
51  30% MPD, 0.1 M Na Acetate pH 4.6, 0.2 M Sodium Chloride
52  30% MPD, 0.1 M Na Acetate pH 4.6, 0.1 M Cadmium Chloride
53  2.0 M Ammonium Sulfate, 0.1 M Na acetate pH 5.6, 0.2 M K/Na Tartrate
54  1.0 M Lithium Sulfate, 0.1 M Na acetate pH 5.6, 0.5 M Ammonium Sulfate
55  35% tert-Butanol, 0.1 M Na acetate pH 5.6
56  1.6 M Magnesium Sulfate, 0.1 M MES pH 6.5
57  12% MPD, 0.1 M MES pH 6.5
58  10% Dioxane, 0.1 M MES pH 6.5, 1.6 M Ammonium Sulfate
59  1.8 M Ammonium Sulfate, 0.1 M MES pH 6.5, 0.01 M Cobalt Chloride
60  1.6 M Sodium acetate pH 6.5
61  30% MPD, 0.1 M Hepes pH 7.5, 0.5 M Ammonium Sulfate
62  15% MPD, 0.1 M Hepes pH 7.5
63  1.6 M Ammonium Sulfate, 0.1 M Hepes pH 7.5, 0.1 M Sodium Chloride
64  2.0 M Ammonium Formate, 0.1 M Hepes pH 7.5
65  1.0 M Sodium Acetate, 0.1 M Hepes pH 7.5, 0.05 M Cadmium Sulfate
66  4.3 M Sodium Chloride, 0.1 M Hepes pH 7.5
67  25% tert-Butanol, 0.1 M Tris pH 8.5
68  1.0 M Lithium Sulfate, 0.1 M Tris pH 8.5, 0.01 M Nickel (II) Chloride
69  12% Glycerol, 0.1 M Tris pH 8.5, 1.5 M Ammonium Sulfate
70  44. 20% Ethanol, 0.1 M Tris pH 8.5

TABLE 1-continued

Figure 6:
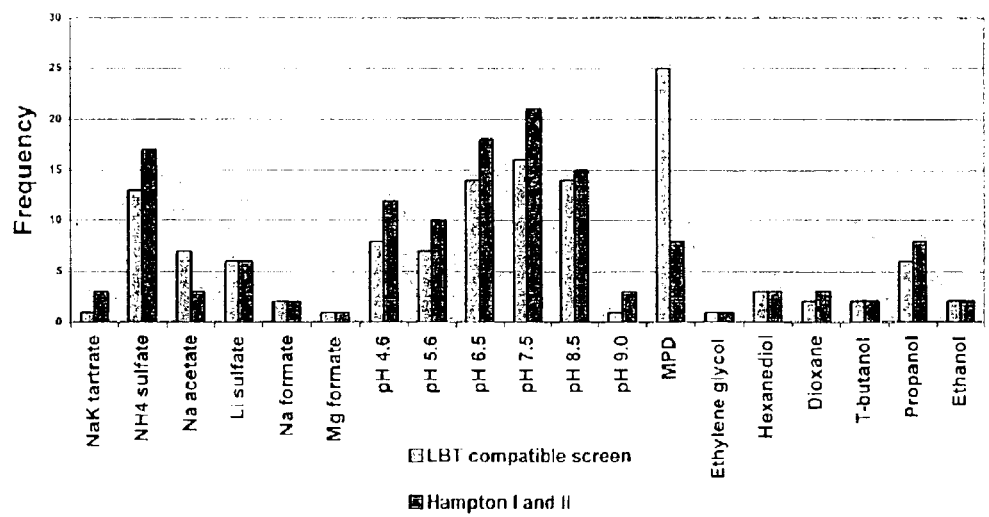
FIG. 6 is graph depicting the frequency of each precipitant in the matrix (or screen) as well as its distribution among the pH values.

LBT-Compatible Matrix 71 47. 2.0 M Magnesium Chloride, 0.1 M Bicine pH 9.0
72 48. 10% MPD, 0.1 M Bicine pH 9.0, 2% Dioxane These new conditions were then analyzed in order to assure that crystallization space was sampled in the same way as in the original screens. The frequency of salts, precipitants and pH values of buffers were tracked. As shown in FIG. 6 the frequency of each precipitant in the screen as well as its distribution among the pH values was not significantly different from that of the original screens. This is partially due to the fact that there are redundancies of representation in the original screen. It should be noted that other successful screens (such as the Hampton Research Cryo Screen) have been designed which remove or replace interfering reagents.

Of course, empirical testing of many different types of target macromolecules can only validate any new screen for macromolecular crystallization. In this case, the coverage of crystallization space will be tested by the ability of the screen to produce crystals of proteins that have already been crystallized. The five representative proteins chosen are selected from the proteins tested by Jancarik and Kim, and include lysozyme, trypsin, ribonuclease A, catalase, papain, and insulin. These proteins are commercially available, cover a wide range of molecular weights (13.7–247.5 kDa) and all crystallize under several different conditions. The utility of the screen in producing crystals of LBT-proteins can only be tested with LBT-protein conjugates.

Structure Determination of LBT-Protein Conjugates

In order to assess the effect of the LBTs on protein structure, four LBT-protein conjugates will be constructed and subjected to structure determination via macromolecular X-ray crystallography. Structure determination will be accomplished by three-wavelength MAD phasing directly on the Ln ion present in the LBT (specifically $Tb^{3+}$). This approach will serve the dual purpose of assessing the effects of the LBT on secondary, tertiary, and quaternary structure while simultaneously evaluating the ability of the LBT metal ion to act as the sole source of phasing power in structure determination. Since it is of interest to apply the LBTs to high-throughput crystallography, automated chain tracing of the experimentally phased electron-density maps (using the program XFIT (McRhee, D. E. *Practical Protein Crystallography;* Academic Press: Boston, 1993)) will always be attempted. Four LBT-protein conjugates have been selected to probe various possible effects of the LBT on structure/function.

1. LBT-N-Ubiquitin and Ubiquitin with the LBT added to the C-terminus (LBT-C-ubiquitin)
2. HIV protease with the LBT added to the N-terminus (LBT-N-HIV protease)
3. Aspartate transcarbamylase (ATCase) with the LBT added to the N-terminus of the catalytic domain (LBT-N-ATCase).
4. RNAse S/S-peptide with the LBT at the N-terminus and C-terminus of the S-peptide Both RNAse A and ubiquitin constructs will provide examples of a small, monomeric proteins and the comparison of the LBT-conjugates with the native structures will be used to test for effects of the site of linkage on the protein. Since the active site of HIV protease is at the subunit interface of this homodimeric protein, LBT-HIV protease will act as an extremely sensitive model to test for effects of the LBT on quaternary structure. Likewise the structure of ATCase will be used as a test case for any effect of the LBT on oligomerization. The X-ray structure determination of LBT-N-HIV and LBT-N-ATCase will be complemented by determination of kinetic parameters to detect any effect of the LBT on catalysis.

If there is significant interference of the LBT with protein activity, folding, or oligomerization, this information will be taken into consideration in the next round of LBT design. Since the Ln-bound LBT will be a stably folded motif, the most likely reason for interference with folding or oligomerization is negative interaction with the surface of the protein to which the LBT is conjugated. This prediction identifies an additional cluster of amino acids to be optimized in the LBT; those that are not directly involved in metal-binding or fluorescence, but instead have side chains that are solvent accessible and thus present a binding surface to the protein linked to the LBT.

HIV Protease

HIV protease is a member of the pepsin-like family of aspartyl proteases. Crystal structures of the HIV protease show that the active site is formed at the interface of the dimer (FIG. 6)(Wlodawer, et al., *Science* 1989, 245, 616–621). The nature of this active site at the interface makes HIV protease a good model system to detect any interference of the LBTs with protein oligomerization. The LBT-HIV protease construct will be made using a synthetic HIV-protease gene expressed in *E. coli*. The LBT-HIV protease will be assayed using a fluorogenic substrate (Molecular Probes) as previously described.(Wang, et al., *Biochem. Biophys. Res. Commun.* 1990, 31, 6493–6496)

ATCase

*E. coli* ATCase catalyzes the condensation of carbamoyl phosphate and L-aspartate to form N-carbamoyl-L-aspartate and inorganic phosphate. The enzyme has become a model system for the study of allosteric regulation. The enzyme shows homotropic cooperativity for the substrate L-aspartate and is heterotropically regulated by ATP and CTP (Wild, et al., *Proc. Natl. Acad. Sci. USA* 1989, 86,46–50). The holoenzyme from *E. coli* is a dodecamer composed of six catalytic chains (C subunit) of 34 kDa molecular weight, and six regulatory chains (R subunit) of 17 kDa molecular weight. Allosteric regulation is modulated by differences in the relative positions of subunits with respect to each other.

We have chosen to construct the conjugate protein with the LBT on the N-terminus of the C subunit since this subunit has previously been expressed and found to be active with a His tag on the amino terminus (Sakash, et al., *J. Biol. Chem.* 2000, 275, 28701–28707). The plasmids for expression of the C and R subunits of ATCase are available. ATCase activity will be measured by a colorimetric method and allosteric behaviour assessed as described previously.

RNAse S

In preliminary studies, the effect of the LBT on the nuclease function of RNAse S was evaluated using the S-protein/S-peptide system (Raines, R. T. *Chem. Rev.* 1998, 98, 1045–1066) wherein the S-peptide was alternately modified with an LBT at either the N- or C-terminus. Kinetic analysis revealed that the LBT had a modest effect on catalytic activity that could probably be attributed to interference of the $Tb^{3+}$ with the substrate. In the future, the catalytically active S-protein/S-peptide complex will serve as a useful device for testing new LBT motifs since S-peptide analogs can be easily prepared using chemical synthesis. The S-protein/S-peptide system will also be used as a prototype for using LBT-protein conjugates in the analysis of protein/ligand interactions.

Example 5

Figure 5:
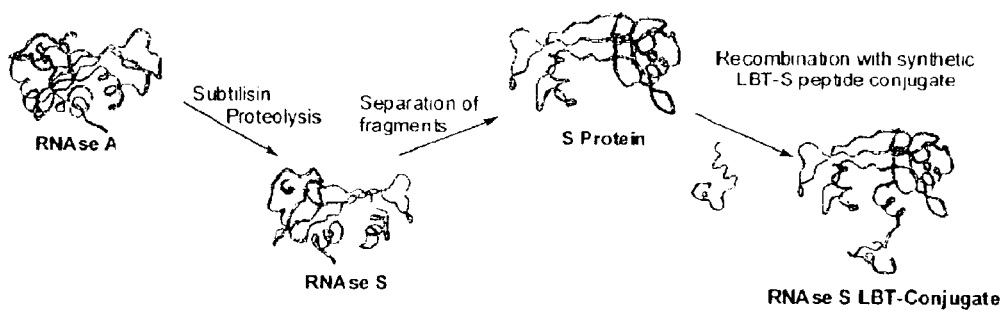
FIG. 5 is a schematic showing the preparation of semi-synthetic LBT-RNAse conjugates.

RNAse S-Protein/LBT-S-Peptide a Model System for Assessing the Utility of the LBT in Studying Protein/Protein Interactions Bovine pancreatic ribonuclease A (RNAse A) is a well-characterized enzyme. (Raines, R. T. *Chem. Rev.* 1998, 98, 1045–1066). The protein comprises a single chain of 124 amino acids which, when subject to limited proteolysis with subtilisin, is cleaved into two fragments, the S-peptide consisting of the first 20 amino-acid residues and the S-protein. These fragments are easily separated and purified under denaturing conditions and when recombined, associate with high affinity ($K_D$ $10^{-6}$–$10^{-7}$M) to afford catalytically-active ribonuclease S (RNAse S)(Connelly, et al., *Biochemistry* 1990, 29, 6108–6114)(FIG. 5). Because the S-protein can be complexed with many analogs of the S-peptide (Kim & Raines, *Anal. Biochem.* 1994, 219, 165–166), this non-covalent, semi-synthetic protein construct represents an ideal model system to determine: 1) the impact of the LBT sequence on the interaction of the S-peptide with the S-protein by monitoring binding and activity, 2) the effects of the protein on the photophysical properties of the LBT and 3) the effect of terbium on enzyme catalysis. Furthermore, this system allows for a rapid "cassette" approach to studying novel LBT sequences in the context of a biological macromolecule, via facile chemical synthesis of any LBT S-peptide fusion desired and complementation with the S-protein. Two LBT tagged S-peptide analogs were prepared with the sequence of LBT1 at the N-terminus (LBT-GPPP-S-Peptide and LBT-PP-S-Peptide-PP, respectively). In both cases, a small, proline-rich spacer sequence was incorporated between the LBT1 and the S-peptide sequence.

Steady-state fluorescence experiments of the LBT-S-peptide fusions indicated minimal impact of the fusion on the terbium fluorescence compared to LBT1 (see Table 2).

µM) exactly as desired for a non-perturbing biological tag. The affinity constants do indicate some dependence on the spacer between the S-peptide and LBT sequence; future experiments comparing other linking sequences will explore the impact of the linker region.

The catalytic activity of the reconstituted enzymes was evaluated based upon the cleavage of a highly sensitive fluorescent RNA substrate (Keleman, et al., *Nucleic Acid Res.* 1999, 27, 3696–3701). These studies indicate that the S-protein/LBT-S-peptide construct has similar catalytic activity to the native RNAse S in the absence of $Tb^{+3}$. The presence of terbium in the assay does however affect the activity of both the RNAse S and the RNAse S-LBT constructs, reducing their activity 3-fold in the presence of 20 µM $Tb^{+3}$. This effect is likely due to the affinity of terbium for the phosphate ligands that are found in the RNAse substrate. It is anticipated that future generations of the LBT sequence with higher affinity for terbium will minimize this type of complication.

The Pro-S/LBT-S-Peptide cassette approach to evaluating LBT sequences demonstrates that the LBT has little influence on this protein/protein interaction and that the LBT is robust enough to retain its $Tb^{+3}$ affinity in the context of a macromolecule. The activity of RNAse S in the presence of concentrations of $Tb^{+3}$ high enough to saturate the LBT reduced the rate of RNA hydrolysis of both native and LBT construct. This aspect of the system could be used in the future evaluation of new LBTs, as it affords a quantitative indication of the influence $Tb^{+3}$ on the activity of enzymes that use phosphate-based substrates.

Example 6

Utilization of the LBT as a Visualization Tool for Protein Expression and Purification The LBT tag can be used for direct observation of protein expression in crude cell lysates. The CC2 sequence, which is a cysteine constrained variant of LBT1, was made alone via peptide synthesis for initial fluorescent characterization and then in the context of the ubiquitin construct already described in place of LBT1 (see FIG. 1 for construct). The

TABLE 2

THERMODYNAMIC PROPERTIES OF S-PEPTIDE/S-PROTEIN INTERACTIONS DETERMINED BY ISOTHERMAL TITRATION CALORIMETRY

| PEPTIDE | Fluorescence Relative to LBT1 | $K_D$ S Peptide/ S-Protein | $K_D$ $Tb^{3+}$ S-Peptide | $K_D$ $Tb^{3+}$ [S-Peptide/S-protein] |
|---|---|---|---|---|
| S-Peptide | N/A | 0.39 µM | N/A | N/A |
| LBT-GPPP-S-Peptide | 96% | 0.30 µM | 6.6 µM | 6.7 µM |
| LBT-PP-S-Peptide | 86% | 0.67 µM | 3.3 µM | 9.6 µM |

The LBT-S-peptide fusions were found to have affinities for the S-protein very similar to the affinities of the native S-peptides (sub-µM affinities). The equilibrium constants of the system were evaluated further using isothermal titration calorimetry, which revealed similar low µM $Tb^{3+}$ affinities for the LBT-S-peptide fusions as for the unmodified LBT 1. The affinity of the LBT site for terbium in the context of the fusion peptide was also unchanged when compared with the unmodified LBT sequences with affinities in the low µM range. Finally the affinity of the S-protein/LBT-S-peptide conjugate for $Tb^{+3}$ is only slightly affected when compared with the fusion peptide alone (3.3 vs. 9.6 µM or 6.6 vs. 6.7

CC2-ubiquitin conjugate can be seen directly on a gel. In fact, 600 ng of protein can be observed by simply soaking the gel in a 1 µM solution of $TbCl_3$ for 10 minutes. Under comparable conditions 4 µg aliquots of calmodulin and S-100 (representative calcium-binding proteins) do not show a signal. Additionally, the LBT-protein conjugate is the only protein to show a signal in the crude cell pellet. It should be emphasized that the limits of detection with a simple hand-held TLC lamp are comparable to a Coomassie stain. Significantly lower limits of detection are achievable with a more sophisticated optical system. Also, this method will be useful for the direct quantitation of protein expression levels. As new LBT sequences are developed it is also likely that improved limits of detection will be achievable. These data demonstrate a very attractive feature of the LBT; the tag can be used for directly observing a target protein conjugate in under 10 minutes without the need for the secondary treatments that are needed for Western blot analysis.

What is claimed is:

1. A method of determining the structure of a peptide, comprising:
    a) expressing a fusion peptide comprising the peptide and a lanthanide binding tag;
    b) isolating said fusion peptide;
    c) forming a crystal of said fusion peptide in the presence of a lanthanide ion; and
    d) determining the two dimensional or three-dimensional crystal structure of the protein,
    wherein the lanthanide binding tag is a peptide that contains: (a) about 12 to about 30 amino acid residues, (b) at least two carboxylic groups and (c) at least one oxygen containing group selected from the group consisting of an backbone carbonyl group, the carboxyl terminus, Ser, Thr, Gln, Asn, or an oxygen of a bound solvent molecule and
    wherein the lanthanide binding tag binds a lanthanide ion with an affinity (KD) of about 1 nM to about 10 μM.

2. The method of claim 1, wherein determining is performed by x-ray crystallography.

3. The method of claim 1, wherein determining is performed by electron microscopy.

4. A method of detecting a peptide comprising:
    a) contacting a sample containing a fusion peptide comprising the peptide and a lanthanide binding tag with a lanthanide ion;
    b) determining the fluorescence of the sample;
    wherein the lanthanide binding tag is a peptide that contains: (a) about 12 to about 30 amino acid residues, (b) at least two carboxylic groups, (c) a fluorophore, and (d) at least one oxygen containing group selected from the group consisting of an backbone carbonyl group, the carboxyl terminus, Ser, Thr, Gln, Asn, or an oxygen of a bound solvent molecule and
    wherein the lanthanide binding tag binds a lanthanide ion with an affinity ($K_D$) of about 1 nM to about 10 μM.

5. The method of claim 4, further comprising c) quantitating the amount of fluorescence of the sample.

6. The method of claim 4, wherein the sample contains a competing ligand which binds in place of the fusion peptide and which alters fluorescence upon binding.

7. The method of claim 6, wherein the fluorescence is altered by about ±-5% or more.

8. The method of claim 7, further comprising determining the binding affinity of the ligand to the second peptide.

9. A method of imaging, comprising:
a) injecting a solution containing a complex of a lanthanide ion and a fusion peptide comprising a peptide and a lanthanide binding tag into a patient;
b) performing imaging on said patient;
wherein the lanthanide binding tag is a peptide that contains: (a) about 12 to about 30 amino acid residues, (b) at least two carboxylic groups and (c) at least one oxygen containing group selected from the group consisting of an backbone carbonyl group, the carboxyl terminus, Ser, Thr, Gln, Asn, or an oxygen of a bound solvent molecule and
wherein the lanthanide binding tag binds the lanthanide ion with an affinity (KD) of about 1 nM to about 10 μM.

10. The method of claim 1, 4 or 9, wherein the lanthanide binding tag has the sequence:
SEQ ID NO. 3: $X^0$-$X^1$-$X^2$-$X^3$-$X^4$-$X^5$-$X^6$-$X^7$-$X^8$-$X^H$-$X^9$-$X^{10}$-$X^{11}$-$X^{12}$-$X^{13}$-$X^{14}$
where $X^0$ and $X^{14}$ are each independently absent or are an amino acid or peptide,
$X^1$, $X^3$, and $X^5$ are each independently an amino acid with a metal binding side chain,
$X^7$ is an amino acid with a fluorophore-containing side chain, and
$X^H$ is absent or is an amino acid or dipeptide,
$X^2$, $X^4$, $X^6$, $X^8$, $X^9$, $X^{10}$, $X^{11}$, $X^{12}$, and $X^{13}$ are each independently an amino acid.

11. The lanthanide-binding peptide of claim 10, which binds a lanthanide ion with an affinity ($K_D$) in the μM range.

12. The lanthanide-binding peptide of claim 11, which binds a lanthanide ion with a $K_D$ in the nM range.

13. The lanthanide-binding peptide of claim 12, which binds a lanthanide ion with a $K_D$ in the pM range.

14. The lanthanide-binding peptide of claim 10, which binds $La^{3+}$, $Eu^{3+}$, $Sm^{3+}$, $Gd^{3+}$, or $Tb^{3+}$.

15. A lanthanide binding peptide comprising an amino acid sequence:
SEQ ID NO. 4: $X^0$-$X^1$-$X^2$-$X^3$-$X^4$-$X^5$-$Gly^6$-$Trp^7$-$X^8$-$X^H$-$Glu^9$-$X^{10}$-$X^{11}$-$Glu^{12}$-$Leu^{13}$-$X^{14}$
where $X^0$ and $X^{14}$ are each independently absent, an amino acid or peptide;
$X^1$ is Asp, Asn, Ser, or Glu,
$X^2$ is Trp, Tyr, Phe, Gln, Ile or Lys,
$X^3$ is Asp, Asn, Ser, or Glu,
$X^4$ is Trp, Tyr, Ala, Gln, Ile or Lys,
$X^5$ is Asp, Asn, Ser, or Glu,
$X^8$ is Trp, Tyr, Phe, Gln, Ile, Lys or Arg,
$X^H$ is absent or is a glycine,
$X^{10}$ is Trp, Tyr, Glu, Asp, Lys or Phe, and
$X^{11}$ is Trp, Tyr, Glu, Asp, Lys or Leu;
wherein the peptide contains 14–30 amino acid residues.

16. A fusion protein comprising a protein and the lanthanide binding peptide of claim 15.

17. A complex comprising the fusion protein of claim 16 and a lanthanide ion.

18. A polynucleotide encoding the lanthanide-binding peptide of claim 15.

19. A polynucleotide encoding the fusion protein of claim 17.

20. A vector comprising the polynucleotide of claim 19 operably linked to a promoter.

21. The lanthanide-binding peptide of claim 15, wherein $X^0$ and $X^{14}$ each are independently a peptide containing a cysteine residue.

* * * * *

UNITED STATES PATENT AND TRADEMARK OFFICE
CERTIFICATE OF CORRECTION

| | | |
|---|---|---|
| PATENT NO. | : 7,101,667 B2 | Page 1 of 1 |
| APPLICATION NO. | : 10/235561 | |
| DATED | : September 5, 2006 | |
| INVENTOR(S) | : Barbara Imperiali et al. | |

It is certified that error appears in the above-identified patent and that said Letters Patent is hereby corrected as shown below:

In the Specification:

At column 1, line 5, please add the following paragraph:

STATEMENT REGARDING FEDERALLY SPONSORED RESEARCH OR DEVELOPMENT

This invention was made with government support under Grant No. F32 GM020510, awarded by the National Institutes of Health. The government has certain rights in the invention.

Signed and Sealed this

Thirty-first Day of May, 2011

David J. Kappos
*Director of the United States Patent and Trademark Office*

SEQUENCE LISTING

```
<160> NUMBER OF SEQ ID NOS: 11

<210> SEQ ID NO 1
<211> LENGTH: 17
<212> TYPE: PRT
<213> ORGANISM: Artificial Sequence
<220> FEATURE:
<223> OTHER INFORMATION: Lanthanide binding tag
<220> FEATURE:
<221> NAME/KEY: MISC_FEATURE
<222> LOCATION: (2)..(2)
<223> OTHER INFORMATION: Xaa is independently an amino acid with a metal
      binding side chain, or can be modified by attaching a peptide,
      which can also be independently absent
<220> FEATURE:
<221> NAME/KEY: MISC_FEATURE
<222> LOCATION: (1)..(1)
<223> OTHER INFORMATION: Xaa is independently absent or is an amino acid
<220> FEATURE:
<221> NAME/KEY: MISC_FEATURE
<222> LOCATION: (4)..(4)
<223> OTHER INFORMATION: Xaa is independently an amino acid with a metal
      binding side chain
<220> FEATURE:
<221> NAME/KEY: MISC_FEATURE
<222> LOCATION: (6)..(6)
<223> OTHER INFORMATION: Xaa is independently an amino acid with a metal
      binding side chain
<220> FEATURE:
<221> NAME/KEY: MISC_FEATURE
<222> LOCATION: (3)..(3)
<223> OTHER INFORMATION: Xaa is independently an amino acid
<220> FEATURE:
<221> NAME/KEY: MISC_FEATURE
<222> LOCATION: (5)..(5)
<223> OTHER INFORMATION: Xaa is independently an amino acid
<220> FEATURE:
<221> NAME/KEY: MISC_FEATURE
<222> LOCATION: (7)..(7)
<223> OTHER INFORMATION: Xaa is independently an amino acid
<220> FEATURE:
<221> NAME/KEY: MISC_FEATURE
<222> LOCATION: (9)..(9)
<223> OTHER INFORMATION: Xaa is independently an amino acid
<220> FEATURE:
<221> NAME/KEY: MISC_FEATURE
<222> LOCATION: (8)..(8)
<223> OTHER INFORMATION: Xaa is independently an amino acid
<220> FEATURE:
<221> NAME/KEY: MISC_FEATURE
<222> LOCATION: (10)..(10)
<223> OTHER INFORMATION: Xaa is absent or is an amino acid
<220> FEATURE:
<221> NAME/KEY: MISC_FEATURE
<222> LOCATION: (11)..(11)
<223> OTHER INFORMATION: Xaa is absent or is an amino acid
<220> FEATURE:
<221> NAME/KEY: MISC_FEATURE
<222> LOCATION: (12)..(12)
<223> OTHER INFORMATION: Xaa is independently an amino acid
<220> FEATURE:
<221> NAME/KEY: MISC_FEATURE
<222> LOCATION: (13)..(13)
<223> OTHER INFORMATION: Xaa is independently an amino acid
<220> FEATURE:
<221> NAME/KEY: MISC_FEATURE
<222> LOCATION: (14)..(14)
<223> OTHER INFORMATION: Xaa is independently an amino acid
<220> FEATURE:
<221> NAME/KEY: MISC_FEATURE
```

```
<222> LOCATION: (15)..(15)
<223> OTHER INFORMATION: Xaa is independently an amino acid
<220> FEATURE:
<221> NAME/KEY: MISC_FEATURE
<222> LOCATION: (16)..(16)
<223> OTHER INFORMATION: Xaa is independently an amino acid, or can be
      modified by attaching a peptide, which can also be independently
      absent
<220> FEATURE:
<221> NAME/KEY: MISC_FEATURE
<222> LOCATION: (17)..(17)
<223> OTHER INFORMATION: Xaa is independently absent or is an amino acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 2
<211> LENGTH: 17
<212> TYPE: PRT
<213> ORGANISM: Artificial Sequence
<220> FEATURE:
<223> OTHER INFORMATION: Lanthanide binding tag
<220> FEATURE:
<221> NAME/KEY: MISC_FEATURE
<222> LOCATION: (2)..(2)
<223> OTHER INFORMATION: Xaa is independently an amino acid with a metal
      binding side chain, or can be modified by attaching a peptide,
      which can also be independently absent
<220> FEATURE:
<221> NAME/KEY: MISC_FEATURE
<222> LOCATION: (1)..(1)
<223> OTHER INFORMATION: Xaa is independently absent or is an amino acid
<220> FEATURE:
<221> NAME/KEY: MISC_FEATURE
<222> LOCATION: (4)..(4)
<223> OTHER INFORMATION: Xaa is independently an amino acid with a metal
      binding side chain
<220> FEATURE:
<221> NAME/KEY: MISC_FEATURE
<222> LOCATION: (6)..(6)
<223> OTHER INFORMATION: Xaa is independently an amino acid with a metal
      binding side chain
<220> FEATURE:
<221> NAME/KEY: MISC_FEATURE
<222> LOCATION: (3)..(3)
<223> OTHER INFORMATION: Xaa is independently an amino acid with a
      fluorophore-containingside chain (preferably Trp)
<220> FEATURE:
<221> NAME/KEY: MISC_FEATURE
<222> LOCATION: (5)..(5)
<223> OTHER INFORMATION: Xaa is independently an amino acid with a
      fluorophore-containing side chain (preferably Trp)
<220> FEATURE:
<221> NAME/KEY: MISC_FEATURE
<222> LOCATION: (7)..(7)
<223> OTHER INFORMATION: Xaa is independently an amino acid with a
      fluorophore-containing side chain (preferably Trp)
<220> FEATURE:
<221> NAME/KEY: MISC_FEATURE
<222> LOCATION: (9)..(9)
<223> OTHER INFORMATION: Xaa is independently an amino acid with a
      fluorophore-containing side chain (preferably Trp)
<220> FEATURE:
<221> NAME/KEY: MISC_FEATURE
<222> LOCATION: (10)..(10)
<223> OTHER INFORMATION: Xaa is absent or is an amino acid
<220> FEATURE:
<221> NAME/KEY: MISC_FEATURE
<222> LOCATION: (11)..(11)
<223> OTHER INFORMATION: Xaa is absent or is an amino acid
<220> FEATURE:
<221> NAME/KEY: MISC_FEATURE
<222> LOCATION: (8)..(8)
<223> OTHER INFORMATION: Xaa is independently an amino acid with a
```

```
        fluorophore-containing side chain (preferably Trp)
<220> FEATURE:
<221> NAME/KEY: MISC_FEATURE
<222> LOCATION: (12)..(12)
<223> OTHER INFORMATION: Xaa is independently an amino acid with a
        fluorophore-containing side chain (preferably Trp)
<220> FEATURE:
<221> NAME/KEY: MISC_FEATURE
<222> LOCATION: (13)..(13)
<223> OTHER INFORMATION: Xaa is independently an amino acid with a
        fluorophore-containing side chain (preferably Trp)
<220> FEATURE:
<221> NAME/KEY: MISC_FEATURE
<222> LOCATION: (14)..(14)
<223> OTHER INFORMATION: Xaa is independently an amino acid with a
        fluorophore-containing side chain (preferably Trp)
<220> FEATURE:
<221> NAME/KEY: MISC_FEATURE
<222> LOCATION: (15)..(15)
<223> OTHER INFORMATION: Xaa is independently an amino acid with a
        fluorophore-containing side chain (preferably Trp)
<220> FEATURE:
<221> NAME/KEY: MISC_FEATURE
<222> LOCATION: (16)..(16)
<223> OTHER INFORMATION: Xaa is independently an amino acid with a
        fluorophore-containing side chain (preferably Trp), or can be
        modified by attaching a peptide, which can also be independently
        absent
<220> FEATURE:
<221> NAME/KEY: MISC_FEATURE
<222> LOCATION: (17)..(17)
<223> OTHER INFORMATION: Xaa is independently absent or is an amino acid

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 3
<211> LENGTH: 17
<212> TYPE: PRT
<213> ORGANISM: Artificial Sequence
<220> FEATURE:
<223> OTHER INFORMATION: Lanthanide binding tag
<220> FEATURE:
<221> NAME/KEY: MISC_FEATURE
<222> LOCATION: (2)..(2)
<223> OTHER INFORMATION: Xaa is independently an amino acid with a metal
        binding side chain, or can be modified by attaching a peptide,
        which can also be independently absent
<220> FEATURE:
<221> NAME/KEY: MISC_FEATURE
<222> LOCATION: (1)..(1)
<223> OTHER INFORMATION: Xaa is independently absent or is an amino acid
<220> FEATURE:
<221> NAME/KEY: MISC_FEATURE
<222> LOCATION: (4)..(4)
<223> OTHER INFORMATION: Xaa is independently an amino acid with a metal
        binding side chain
<220> FEATURE:
<221> NAME/KEY: MISC_FEATURE
<222> LOCATION: (6)..(6)
<223> OTHER INFORMATION: Xaa is independently an amino acid with a metal
        binding side chain
<220> FEATURE:
<221> NAME/KEY: MISC_FEATURE
<222> LOCATION: (3)..(3)
<223> OTHER INFORMATION: Xaa is independently an amino acid
<220> FEATURE:
<221> NAME/KEY: MISC_FEATURE
<222> LOCATION: (5)..(5)
<223> OTHER INFORMATION: Xaa is independently an amino acid
<220> FEATURE:
<221> NAME/KEY: MISC_FEATURE
<222> LOCATION: (7)..(7)
<223> OTHER INFORMATION: Xaa is independently an amino acid
```

```
<220> FEATURE:
<221> NAME/KEY: MISC_FEATURE
<222> LOCATION: (9)..(9)
<223> OTHER INFORMATION: Xaa is independently an amino acid
<220> FEATURE:
<221> NAME/KEY: MISC_FEATURE
<222> LOCATION: (10)..(10)
<223> OTHER INFORMATION: Xaa is absent or is an amino acid
<220> FEATURE:
<221> NAME/KEY: MISC_FEATURE
<222> LOCATION: (11)..(11)
<223> OTHER INFORMATION: Xaa is absent or is an amino acid
<220> FEATURE:
<221> NAME/KEY: MISC_FEATURE
<222> LOCATION: (12)..(12)
<223> OTHER INFORMATION: Xaa is independently an amino acid
<220> FEATURE:
<221> NAME/KEY: MISC_FEATURE
<222> LOCATION: (13)..(13)
<223> OTHER INFORMATION: Xaa is independently an amino acid
<220> FEATURE:
<221> NAME/KEY: MISC_FEATURE
<222> LOCATION: (14)..(14)
<223> OTHER INFORMATION: Xaa is independently an amino acid
<220> FEATURE:
<221> NAME/KEY: MISC_FEATURE
<222> LOCATION: (15)..(15)
<223> OTHER INFORMATION: Xaa is independently an amino acid
<220> FEATURE:
<221> NAME/KEY: MISC_FEATURE
<222> LOCATION: (16)..(16)
<223> OTHER INFORMATION: Xaa is independently an amino acid, or can be
      modified by attaching a peptide, which can also be independently
      absent
<220> FEATURE:
<221> NAME/KEY: MISC_FEATURE
<222> LOCATION: (17)..(17)
<223> OTHER INFORMATION: Xaa is independently absent or is an amino acid
<220> FEATURE:
<221> NAME/KEY: MISC_FEATURE
<222> LOCATION: (8)..(8)
<223> OTHER INFORMATION: Xaa is an amino acid with a fluorophore-
      containing side chain (preferably Trp)

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 4
<211> LENGTH: 16
<212> TYPE: PRT
<213> ORGANISM: Artificial Sequence
<220> FEATURE:
<223> OTHER INFORMATION: Lanthanide binding tag
<220> FEATURE:
<221> NAME/KEY: MISC_FEATURE
<222> LOCATION: (2)..(2)
<223> OTHER INFORMATION: Xaa is Asp, Asn, Ser, or Glu, or can be
      modified by attaching a peptide, which can also be independently
      absent
<220> FEATURE:
<221> NAME/KEY: MISC_FEATURE
<222> LOCATION: (1)..(1)
<223> OTHER INFORMATION: Xaa is independently absent or is an amino acid
<220> FEATURE:
<221> NAME/KEY: MISC_FEATURE
<222> LOCATION: (3)..(3)
<223> OTHER INFORMATION: Xaa is Trp, Tyr, Phe, Gln, Ile, or Lys
<220> FEATURE:
<221> NAME/KEY: MISC_FEATURE
<222> LOCATION: (4)..(4)
<223> OTHER INFORMATION: Xaa is Asp, Asn, Ser, or Glu
<220> FEATURE:
<221> NAME/KEY: MISC_FEATURE
<222> LOCATION: (5)..(5)
```

```
<223> OTHER INFORMATION: Xaa is Trp, Tyr, Ala, Gln, Ile, or Lys
<220> FEATURE:
<221> NAME/KEY: MISC_FEATURE
<222> LOCATION: (6)..(6)
<223> OTHER INFORMATION: Xaa is Asp, Asn, Ser, or Glu
<220> FEATURE:
<221> NAME/KEY: MISC_FEATURE
<222> LOCATION: (9)..(9)
<223> OTHER INFORMATION: Xaa is Trp, Tyr, Phe, Gln, Ile, Lys, or Arg
<220> FEATURE:
<221> NAME/KEY: MISC_FEATURE
<222> LOCATION: (10)..(10)
<223> OTHER INFORMATION: Xaa is is absent or is a glycine
<220> FEATURE:
<221> NAME/KEY: MISC_FEATURE
<222> LOCATION: (12)..(12)
<223> OTHER INFORMATION: Xaa is Trp, Tyr, Glu, Asp, Lys, or Phe
<220> FEATURE:
<221> NAME/KEY: MISC_FEATURE
<222> LOCATION: (13)..(13)
<223> OTHER INFORMATION: Xaa is Trp, Tyr, Glu, Asp, Lys, or Leu
<220> FEATURE:
<221> NAME/KEY: MISC_FEATURE
<222> LOCATION: (15)..(15)
<223> OTHER INFORMATION: Leu can be modified by attaching a peptide,
      which can also be independently absent
<220> FEATURE:
<221> NAME/KEY: MISC_FEATURE
<222> LOCATION: (16)..(16)
<223> OTHER INFORMATION: Xaa is independently absent or is an amino acid

<400> SEQUENCE: 4

Xaa Xaa Xaa Xaa Xaa Xaa Gly Trp Xaa Xaa Glu Xaa Xaa Glu Leu Xaa
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Lanthanide-binding peptide

<400> SEQUENCE: 5

Gly Asp Tyr Asn Lys Asp Gly Trp Tyr Glu Glu Leu Glu Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Lanthanide-binding peptide

<400> SEQUENCE: 6

Gly Asp Tyr Asn Lys Asp Gly Trp Tyr Glu Phe Tyr Glu Leu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Lanthanide-binding peptide

<400> SEQUENCE: 7

Gly Asp Phe Asn Gln Asp Gly Trp Ile Glu Glu Leu Glu Leu
1               5                   10

<210> SEQ ID NO 8
<211> LENGTH: 14
<212> TYPE: PRT
```

```
<213> ORGANISM: Artificial Sequence
<220> FEATURE:
<223> OTHER INFORMATION: Lanthanide-binding peptide

<400> SEQUENCE: 8

Gly Asp Phe Asn Lys Asp Gly Trp Ile Glu Phe Tyr Glu Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Lanthanide-binding peptide

<400> SEQUENCE: 9

Gly Asp Ile Asn Lys Asp Gly Trp Phe Glu Phe Tyr Glu Leu
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Lanthanide Binding Tag

<400> SEQUENCE: 10

Ala Cys Ala Asp Tyr Asn Lys Asp Gly Trp Tyr Glu Glu Leu Glu Cys
1               5                   10                  15
Ala Ala

<210> SEQ ID NO 11
<211> LENGTH: 14
<212> TYPE: PRT
<213> ORGANISM: Artificial Sequence
<220> FEATURE:
<223> OTHER INFORMATION: Lanthanide binding tag 1

<400> SEQUENCE: 11

Gly Asp Tyr Asn Lys Asp Gly Trp Tyr Glu Glu Leu Glu Leu
1               5                   10
```